US011433102B2

(12) United States Patent
Borody

(10) Patent No.: US 11,433,102 B2
(45) Date of Patent: Sep. 6, 2022

(54) COMPOSITIONS AND METHODS FOR TREATING PARKINSON'S DISEASE (PD) AND RELATED DISORDERS

(71) Applicant: Finch Therapeutics Holdings LLC, Somerville, MA (US)

(72) Inventor: Thomas J. Borody, Five Dock (AU)

(73) Assignee: Finch Therapeutics Holdings LLC, Somerville, MA (US)

( * ) Notice: Subject to any disclaimer, the term of this patent is extended or adjusted under 35 U.S.C. 154(b) by 0 days.

(21) Appl. No.: 16/603,036

(22) PCT Filed: Apr. 4, 2018

(86) PCT No.: PCT/US2018/026080
§ 371 (c)(1),
(2) Date: Oct. 4, 2019

(87) PCT Pub. No.: WO2018/187467
PCT Pub. Date: Oct. 11, 2018

(65) Prior Publication Data
US 2020/0188442 A1 Jun. 18, 2020

Related U.S. Application Data

(60) Provisional application No. 62/511,740, filed on May 26, 2017, provisional application No. 62/482,162, filed on Apr. 5, 2017.

(51) Int. Cl.
*A61K 35/38* (2015.01)
*A61P 25/16* (2006.01)

(52) U.S. Cl.
CPC .............. *A61K 35/38* (2013.01); *A61P 25/16* (2018.01)

(58) Field of Classification Search
CPC .................................................... A61P 25/16
See application file for complete search history.

(56) References Cited

U.S. PATENT DOCUMENTS

| | | |
|---|---|---|
| 3,192,116 A | 6/1965 | Mose et al. |
| 3,320,130 A | 5/1967 | Henry |
| 3,713,836 A | 1/1973 | Carlsson |
| 4,098,728 A | 7/1978 | Rosenblatt |
| 4,309,782 A | 1/1982 | Paulin |
| 4,332,790 A | 6/1982 | Sozzi et al. |
| 4,335,107 A | 6/1982 | Snoeyenbos et al. |
| 4,394,377 A | 7/1983 | Spires |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems, 10th Revision (ICD-10)-WHO Version, Chapter 1*, pp. 1 (2016) <www.apps.who.int/classifications/icd1 0/browse/2016/en#II>.
"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).

(Continued)

*Primary Examiner* — Qiwen Mi
(74) *Attorney, Agent, or Firm* — Arnold & Porter Kaye Scholer LLP

(57) ABSTRACT

The present disclosure is in the field of pharmaceutical compositions suitable for the treatment of diseases in mammals. The disclosure provides novel compositions comprising non-pathogenic fecal microbes or a sterile fecal filtrate for treating Parkinson's disease and related diseases. The disclosure also provides methods for treating a subject with the compositions disclosed herein.

24 Claims, No Drawings

(56) References Cited

U.S. PATENT DOCUMENTS

| | | |
|---|---|---|
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,586,029 B2 | 11/2013 | Kasper et al. |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,719,144 B2 | 8/2017 | Krajmalnik-Brown et al. |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2009/0312436 A1* | 12/2009 | Levy .................. A61P 25/16 514/657 |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookaa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2014/0363398 A1* | 12/2014 | Jones .................. A61K 35/744 424/93.4 |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0199425 A1* | 7/2016 | Lue .................. A61K 38/482 424/93.45 |
| 2016/0279178 A1 | 9/2016 | Borody |
| 2016/0279179 A1 | 9/2016 | Borody |
| 2016/0331791 A1* | 11/2016 | Borody .................. A61P 1/04 |
| 2016/0339065 A1 | 11/2016 | Adams et al. |
| 2017/0216378 A1 | 8/2017 | Honda et al. |
| 2017/0246220 A1 | 8/2017 | Sato et al. |
| 2017/0348360 A1 | 12/2017 | Borody |
| 2018/0153943 A1 | 6/2018 | Borody |
| 2018/0256652 A1 | 9/2018 | Borody |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1271674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| KR | 10-0913405 B1 | 8/2009 |
| WO | WO 90/01335 A1 | 2/1990 |

(56) References Cited

FOREIGN PATENT DOCUMENTS

| | | |
|---|---|---|
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2012/013861 A2 | 2/2012 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2013/037067 A1 | 3/2013 |
| WO | WO 2013/090825 A1 | 6/2013 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 2/2016 |
| WO | WO 2016/183577 A1 | 11/2016 |
| WO | WO 2016/191356 A1 | 12/2016 |
| WO | WO 2017/075098 A1 | 5/2017 |
| WO | WO 2017/152137 A2 | 9/2017 |

OTHER PUBLICATIONS

"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pelf>.

"Frequently Asked Questions about Clostridium difficile for Healthcare Providers," Healthcare-associated Infections (HAis), Centers for Disease Control and Prevention, pp. 1-6, Nov. 25, 2010, updated Mar. 6, 2012, Web, May 19, 2014 <http://www.cdc.gov/HAI/organisms/cdiff/Cdiff faqs HCP.html>.

"Functional Anatomy of Prokaryotic and Eukaryotic Cells," printed Mar. 16, 2017 <http://classes.midlandstech.edu/carterp/courses/bio225/chap04/lecture2.htm>.

"Monilia," Def. 1, Stedman's Medical Dictionary, n.d., Web, Nov. 22, 2005.

"Probiotic," Def. 1, MSN Encarta—Dictionary, Encarta, n.d., Web, Dec. 1, 2005.

Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).

Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).

Acha et al., "Changes of viability and composition of the *Escherichia coli* flora in faecal samples during long time storage," Journal of Microbiological Methods, Elsevier, 63(3):229-238 (2005).

Agrawal et al., "'Global warming' to *Mycobacterium avium* subspecies paratuberculosis," *Future Microbial*, 9(7):829-832 (2014).

Agrawal et al., "A Long-Term Follow-Up Study of the Efficacy and Safety of Fecal Microbiota Transplant (FMT) for Recurrent/Severe/Complicated *C. dificile* Infection (CDI) in the Elderly," *Gastroenterol*, 146(5)(Suppl 1):S42-43 (2014).

Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).

Akao et al., "A Purgative Action of Barbaloin Is Induced by *Eubacterium* sp. Strain BAR, a Human Intestinal Anaerobe, Capable of Transforming Barbaloin to Aloe-EmodinAnthrone," Biol. Pharm., 19(1):136-138 (1996).

Al-Eidan et al., "Clostridium difficile-associated diarrhoea in hospitalised patients," *J Clin. Pharm. Ther.*, 25(2):101-109 (2000).

Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).

Amand et al., "Epidemiology, clinical manifestations, and outcome of Clostridium difficile-associated diarrhea," *Am J Gatroenterol.*, 89(4):519-23 (1994).

Ananthakrishnan et al., "Express hospitalisation burden associated with Clostridium difficile in patients with inflammatory bowel disease," *Gut*, 57(2):205-210 (2007).

Anderson et al., "Systematic review: faecal microbiota transplantation in the management of inflammatory bowel disease," *Aliment. Pharmacol. Ther.*, 36:503-16 (2012).

Andoh et al., "Terminal restriction fragment polymorphisum analyses of fecal microbiota in five siblings including two with ulcerative colitis," *Journal of Clinical Gastroenterology*, 2:343-345 (2009).

Andeweg et al., "Guidelines of Diagnostic and Treatment of Acute Left-Sided Colonic Diverticulitis," Digestive Surgery 30:278-292 (2013).

Andrews et al., "'Putting back the bugs': Bacterial Treatment Relieves Chronic Constipation and Symptoms of Irritable Bowel Syndrome," *Med. J Aust.*, 159(9):633-634 (1993).

Andrews et al., "Bacteriotherapy for Chronic Constipation—A Long Term Follow-Up," *Gastroenterol*, 108:A563 Abstract (1995).

Andrews et al., Chronic Constipation (CC) may be reversed by "Bacteriotherapy," *Gastroenterol*, 106:A459 (1994).

Andrews et al., "Chronic constipation reversed by restoration of bowel flora. A case and a hypothesis," *European Journal of Gastroenterology & Hepatology*, 4:245-247 (1992).

Anorexia nervosa, Encyclopedia Index A, health AtoZ, Medical Network, Inc., pp. 1-7, n.d., Web, Nov. 23, 2005 <http://www.healthatoz.com/healthatoz/Atoz/ency/anorexia_nervosa.jsp>.

Arkkila et al., "Fecal Bacteriotherapy for Recurrent *Clostridium difficile* Infection," *Gastroenterology*, 138(5):SI-S5 (2010).

Aroniadis et al., "Intestinal Microbiota and the Efficacy of Fecal Microbiota Transplantation in Gastrointestinal Disease," Gastroenterology and Hepatology, 10(4):230-7 (2014).

Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).

Atarashi et al., "Induction of Colonic Regulatory T Cells by Indigenous *Clostridium* Species," *Science*, 331(6015):337-341, published online Dec. 23, 2010.

Atarashi et al., "$T_{reg}$ induction by a rationally selected mixture of *Clostridia* strains from the human microbiota," *Nature*, 500(7461):232-236 (2013).

Atarashi et al., "WS/PP-064-03 Regulation of colonic regulatory T cells by *Clostridium* species," *International Immunology*, 22(Suppl 1, Part 3), pp. 1-3, (2010).

Atarashi et al., WS-064 Musosal immunity:homeostasis, 14thICIC Abstract book, 14th International Congress of lmmunology, pp. iiil31-iiil33 (2010).

Autism, Health Encyclopedia—Diseases and Conditions, The Health Scout Network, pp. 1-5, n.d., Web, Nov. 22, 2005 <www.healthscout.com>.

(56) References Cited

OTHER PUBLICATIONS

Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent Clostridium difficile infection," *Anaerobe*, 15(6):2S5-2S9 (2009).
Bakken et al., "Treating Clostridium difficile Infection with Fecal Microbiota Transplantation," *Clinical Gastroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Belkaid et al., "Natural regulatory T cells in infectious disease," *Nature Immunology*, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Bergey's Manual of Systematic Bacteriology, Second Edition, Volume Three, The Firmicutes, pp. 1-16 (2009).
Blaser et al., "What are the consequences of the disappearing human microbiota?" *Nat. Rev. Microbial.*, 7(12):887-894 (2009)
Blaser, "Who are we? Indigenous microbes and the ecology of human diseases," *EMBO Rep*, 7(10):956-960 (2006).
Bolte, "Autism and Clostridium tetani," Medical Hypotheses, 51(2):133-144 (1998).
Bolte, Therapies for Gastrointestinal and Neurological Disorders, U.S. Appl. No. 60/214,813, filed Jun. 28, 2000.
Borody et al., "Fecal microbiota transplantation in gastrointestinal disease: 2015 update and the road ahead," Expert Review of Gastroenterology and Hepatology, 9(11):1379-1391 (2015).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516(2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al., "*Anti-Mycobacterium avium* SS *Paratuberculosis* (MAP) Therapy and Fistula Closure in Patients with Severe Crohn's Disease," *Am J Gast*, Al 0J:S440 (2006).
Borody et al., "Bacteriotherapy in Chronic Fatigue Syndrome (CFS): A retrospective review," *AmJGastro*, 107(SJ):A1481 (2012).
Borody et al., "Bacteriotherapy Using Fecal Flora: toying with human motions" *J Clin. Gastroenterol.*, 38(6):475-483 (2004).
Borody et al., "Bowel-flora alteration: a potential cure for inflammatory bowel disease and irritable bowel syndrome?" *Med. J Aust.*, 150:604 (1989).
Borody et al., "Changes in Crohn's Disease Activity Index and C-Reactive Protein Levels During Anti-MAP Therapy," *AM J Gastro*, 104(S3):A1293 (2009).

Borody et al., "Clostridium *difficile* Complicating Inflammatroy Bowel Disease: Pre- and Post- Treatment Findings," *Gastroenterol*, 134(4)Suppl 1:A-361 (2008).
Borody et al., "Could fecal microbiota transplantation cure all Clostridium difficile infections?," *Future Microbial*, 9:1-3 (2014)
Borody et al., "Entamoeba *histolytica*: another cause of Crohn's Disease," *AM J Gastro*, 104(S3):A990 (2009).
Borody et al., "Faecal bacteriotherapy (FB) for chronic C. *difficile* (Cd) syndromes," *J Gastroenterol Hepatol*, 18(Suppl.) :B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AMJGastro*, 106(S2):A942 (2011).
Borody et al., "Fecal microbiota transplantation and emerging applications," *Nat. Rev. Gastroenterol. Hepatol.*, 9(2):88-96 (2011).
Borody et al., "Fecal microbiota transplantation for *Clostridium difficile* infection: A surgeon's perspective" *Seminars in Colon and Rectal Surgery*, 25:163-166 (2014).
Borody et al., "Fecal microbiota transplantation in gastrointestinal diseases—What practicing physicians should know," *Polish Archives of Internal Medicine*, 125(11):852-858 (2015).
Borody et al., "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Experience," *Am J Gastro*, 107(Supp 1):A1644 (2012).
Borody et al., "Fecal microbiota transplantation: a new standard treatment option for *Clostridium difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Brody et al., "Fecal Microbiota Transplantation: Techniques, Applications, and Issues," *Gastroenterol Clin North Am*, 41:781-803 (2012).
Borody el al., "Irritable Bowel Syndrome and *Dientamoeba fragilis*," *ASM Sydney National Conference*, pp. 4-5 (2002)
Borody et al., "Is Crohn's Disease Ready for Fecal Microbiota Transplantation?," *J Clin Gastroenterol*, 48(7):582-583 (2014).
Borody et al., "Myoclonus-dystonia affected by GI Microbiota?," *AM J Gastro*, 106(S2):A940 (2011).
Borody et al., "Novel appearance of healing mucosa following *anti-Mycobacterium avium paratuberculosis* therapy for Crohn's disease," *J Gastroenterol Hepatol*, 19(Suppl) :A210 (2004).
Borody et al., Reversal of Idiopathic Thrombocytopenic Purpura [ITP] with Fecal Microbiota Transplantation [FMT], *AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, *2015 ACG Annual Scientific Meeting*, Honolulu, Hawaii, USA (2015).

(56) References Cited

OTHER PUBLICATIONS

Borody et al., "Treatment of Severe Constipation Improves Parkinson's Disease (PD) Symptoms," *AM J Gastro*, 104(S3):A999 (2009).
Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Resulsts at 38-43 Months, *J Gastroenterol & Hepatol*, 15(Suppl.):J102 (2000).
Borody et al., "Treatment of Severe Crohn's disease using antimycobacterial triple therapy—approacing a cure?," *Digest Liver Dis*, 34(1):29-38 (2002).
Borody et al., "Treatment of ulcerative colitis using fecal bacteriotherapy," *J Clin. Gastroenterol.*, 37(1):42-47 (2003)
Borody, "Bacteriotherapy for Chronic Fatigue Syndrome—A Long Term Follow-Up Study," Proceedings of ACMA Complementary Medicine Sydney, p. 1 (1995).
Borody, "Flora Power"—Fecal Bacteria Cure Chronic C. difficile Diarrhoea, *Am J Gastroenterol*, 95(11):3028-3029 (2000).
Borody, "Is the Infected Patient too 'Difficile' to Treat?," The Australian Society for Microbiology 2009 Perth, SY03 & SY03. 1, p. 27 & 56, (2009).
Borody, "Letter to the Editor—Response to Drs. Famularo et al., " *AJG*, 96(7):2262-2264 (2001).
Borriello, "Clostridial Disease of the Gut," Clinical Infectious Diseases, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Endoscopic Fecal Microbiota Transplantation: "First-Line" Treatment for Severe Clostridium difficile Infection?" *J Clin. Gastroenterol.*, 45(8):655-657 (2011).
Brandt et al., "Fecal microbiota transplantation for recurrent *Clostridium difficile* infection," *JClin Gastroenterol.*, 45(Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Brandt et al., Safety of Fecal Microbiota Transplantation (FMT) in Immunocompromised (Ie) Patients with Inflammatory Bowel Disease (IBD), *Am J Gastroenterol*, 108(Suppl 1):S556(2013).
Browne et al., "Culturing of 'unculturable' human microbiota reveals novel taxa and extensive sporulation," *Nature*, 533(7604):543-546 (2016).
Bueche et al., "Quantification of Endospore-Forming Firmicutes by Quantitative PCR with the Functional Gene spo0A," *Applied and Environmental Microbiology*, 79(17):5302-5312(2013).
Cammarota et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammorata et al., "Review article: biofile formation by Helicobacter pylori as a target for eradicatioin of resistant infection," Aliment Pharmacol Ther, 36:222-30 (2012).
Campbell et al., "The many faces of Crohn's Disease: Latest concepts in etiology," *OJIM*, 2(2):107-115 (2012).
Cano et al., "Revival and identification of bacterial spores in 25-40 million year old Dominican Amber Science," Science, 268(5213):1060-1064 (1995).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk-four states, 2005." *Morbidity and Mortality Weekly Report*, 54(47):1201-1205 (2005).
Chamberlain et al., "MAP-associated Crohn's Disease, MAP, Koch's postulates, causality and Crohn's Disease," *Digestive and Liver Disease*, 39:790-794 (2007).

Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J Infect. Dis.*, 197(3):435-438 (2008).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Chibani-Chennoufi et al., "In Vitro and In Vivo Bacteriolytic Activities of *Escherichia coli* Phages: Implications for Phage Therapy," *Antimicrobial Agents and Chemotherapy*, 48(7):2558-2569 (2004).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," *PLOS One*, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010)
Clancy et al., "Anti-MAP Therapy Induces and Maintains Remission in Severe Crohn's Disease," *Ann NY Acad Sci*, p. 1 (2005).
Claus et al., "Colonization-induced host-gut microbial metabolic interaction," *MBio*, 2(2):e00271-00210 (2011).
Claus et al., "Systemic multicompartmental effects of the gut microbiome on mouse metabolic phenotypes," *Mal. Syst. Biol.*, 4(1):219 (2008).
Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).
Collins et al., "The Phylogeny of the Genus *Clostridium*: Proposal of Five New Genera and Eleven New Species Combinations," *International Journal of Systematic Bacteriology*, pp. 812-826 (1994).
U.S. Appl. No. 12/843,409, filed Jul. 26, 2010.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Applied Bacteriology, 34(2):477-483 (1971).
Cutolo et al., "Fecal feedings as a therapy in *Staphylococcus enterocolitis,*" *NY State J Med*, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," J. Med Microbiology, 28:151-154 (1989).
De Giulio et al., "Use of Alginate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," *Drug Develop. & Indust. Pharm.*, 31:677-685 (2005).
Definition of Kit, Merriam-Webster, pp. 1-10., Web., 2019 <https://www.merriam-webster.com/dictionary/kit>.
Dendukuri et al., "Probiotic therapy for the prevention and treatment of Clostridium difficile-associated diarrhea: a systematic review," *CMAJ*, 173(2):167-170 (2005).
Derwent Abstract Accession No. 98-230427/20, WO 98/13068 A, (Kuperman VB) Apr. 2, 1998.

(56) References Cited

OTHER PUBLICATIONS

Dethlefsen et al., "An ecological and evolutionary perspective on human-microbe mutualism and disease," Nature, 449(7164):811-818 (2007).
Dewhirst et al., "Phylogeny of the Defined Murine Microbiota: Altered Schaedler Flora," Applied and Environmental Microbiology, 65(8):3287-3292 (1999).
DuPont, "The search for effective treatment of Clostridium difficile infection," N Engl J Med., 364(5):473-475 (2011).
Eckburg et al., "Diversity of the human intestinal microbial flora," Science, 308(5728):1635-1638 (2005).
Eiseman et al., "Fecal enema as an adjunct in the treatment of pseudomembranous enterocolitis," Surgery, 44(5):854-859 (195 8).
Eller et al., "Anaerobic Roll Tube Media for Nonselective Enumeration and Isolation and Bacteria in Human Feces," Applied Microbiology, 22(4):522-529 (1971).
Extended European Search Report dated Apr. 3, 2014, in European Patent Application No. 11813951.8.
Extended European Search Report dated Mar. 16, 2018, in European Patent Application No. 17203052.0.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," Can J Gastroenterol., 16:A43 (2002).
Fenton et al., "Pseudomembranous colitis assocated with antibiotic therapy—an emerging entity," Can Med Assoc J, 111(10):1110-1111 (1974).
Floch et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010)
Flotterod et al., "Refractory Clostridium difficile infection. Untraditional treatment of antibiotic-induced colitis," Tidsskr Nor Laegeforen, 111:1364-1365 (1991).
Frank et al., "Molecular-phylogenetic characterization of microbial community imbalances in human inflammatory bowel diseases," PNAS, 104(34):13780-13785 (2007).
Frantzen et al., "Empirical evaluation of preservation methods for faecal DNA," Molecular Ecology, 7(10):1423-1428 (1998).
Freeman et al., "The changing epidemiology of Clostridium difficile infections," Clin Microbial. Rev., 23(3):529-549 (2010).
Frese et al., "The evolution of host specialization in the vertebrate gut symbiont Lactobacillus reuteri," PloS Genet., 7(2):e1001314 (2011).
Gaboriau-Routhiau et al., "The Key Role of Segmented Filamentous Bacteria in the Coordinated Maturation of Gut Helper T Cell Responses," Immunity, 31(4):677-689 (2009).
Garborg et al., "Results of faecal donor instillation therapy for recurrent Clostridium difficile-associated diarrhoea," Scand J Infect Dis., 42(11-12):857-61 (2010).
Garey et al., "Meta-analysis to assess risk factors for recurrent Clostridium difficile infection," J Hosp. Infect., 70(4):298-304 (2008).
Gerding, "Management of Clostridium difficile infection: thinking inside and outside the box," Clin Infect Dis., 51(11):1306-13 (2010).
Geuking et al., "Intestinal Bacterial Colonization Induces Mutualistic Regulatory T Cell Responses," Immunity, 34:794-806 (2011).
Gitlin et al., "Mycobacterium avium ss paratuberculosis-associated Diseases: Piecing the Crohn's Puzzle Together," J Clin Gastroenterol, 46(8):649-655 (2012).
Gough et al., "Systematic review of intestinal microbiota transplantation (fecal bacteriotherapy) for recurrent Clostridium difficile infection," Clin. Infect. Dis., 53(10):994-1002 (2011).
Grehan et al., "Durable alteration of the colonic microbiota by the administraion of donor fecal flora," Journal of Clinical Gastroenterology, 44(8):551-561 (2010).
Guarner et al., "Gut flora in health and disease," Lancet, 361(9356):512-519 (2003).

Gustafsson et al., "The Effect of Faecal Enema on Five Microflora-Associated Characteristics in Patients with Antibiotic-Associated Diarrhoea," Scandinavian Journal of Gastroenterology, 34:580-586 (1999)
Gustafsson et al., "Faecal Short-Chain Fatty Acids in Patients with Antibiotic-Associated Diarrhoea, before and after Faecal Enema Treatment," Scand J Gastroenterol, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engrafuinent of gut microbiota following transplantation of gut microbiota following transplantation of previously frozen fecal bacteria," Gut Microbes, 4(2):1-11 (2013).
Hamilton et al., "Standardized Frozen Preparation for Transplantation of Fecal Microbiota for Recurrent Clostridium difficile Infection," Article and Supplementary Material, Am. J. Gastroenterol., 107(5):761-767 (2012).
Hayashi et al., "Phylogenetic Analysis of the Human Gut Microbiota Using 16S rDNA Clone Libraries and Strictly Anaerobic Culture-Based Methods," Microbial. Immunol., 46(8):535-548 (2002).
Hecker et al., "Fecal Microbiota Transplantation by Freeze-Dried Oral Capsules for Recurrent Clostridium difficile Infection," Open Forum Infect Dis, 3(2): 1-2 (2016).
Hellemans et al., "Fecal transplantation for recurrent Clostridium difficile colitis, an underused treatment modality," Acta Gastroenterol Belg., 72(2):269-70 (2009).
Henriksson et al., "Probiotics under the regulatory microscope," Expert Opin. Drug Saf, 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Hoehn et al., "Parkinsonism: onset, progression, and mortality," Neurology 17:427-442 (1967).
Honda et al., "Regulation of T Cell Responses by Intestinal Commensal Bacteria," Journal of Intestinal Microbiology, vol. 25, 2nd Edition:104 (2011).
Hongliang et al., "Freeze-dried, Capsulized Fecal Microbiota Transplantation for Relapsing Clostridium difficile Infection," Journal of Clinical Gastroenterology, 43(6):537-538 (2015).
Hooper et al., "How host-microbial interactions shape the nutrient environment of the mammalian intestine," Annu. Rev. Nutr., 22:283-307 (2002).
Hope et al., "Sporadic colorectal cancer-role of the commensal microbiota," FEMS Microbial. Lett., 244:1-7 (2005).
Hota et al., "Determining Mortality Rates Attributable to Clostridium difficile Infection," Emerg. Infect. Dis., 18(2):305-307 (2012)
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT3 and Foxol," The Journal of Immunology, 3665-3674 (2015).
Hu et al., "Prospective derivation and validation of a clinical prediction rule for recurrent Clostridium difficile infection," Gastroenterology, 136:1206-1214 (2009).
Huang et al., "Once-daily propranolol extended-release tablet dosage form: formulation design and in vitro/in vivo investigation," European J of Pharm. & Biopharm., 58:607-614 (2004).
Huttenhower et al., "Structure, function and diversity of the healthy human microbiome," The Human Microbiome Project Consortium, Nature, 486:207-214 (2012).
Immunology in the 21st Century: Defeating Infection, Autoimmunity, Allergy, and Cancer, ICI 2010 Wrap-up Report, 14th International Congress of lmmunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowel/chrohns.html>.

(56) References Cited

OTHER PUBLICATIONS

Information Disclosure Statement filed Nov. 28, 2017, in U.S. Appl. No. 15/487,553.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion (WO) dated Feb. 2, 2018 in International Application No. PCT/US2017/055618.
International Search Report and Written Opinion (WO) dated February 2, 2018 in International Application No. PCT/US2017/056131.
International Search Report and Written Opinion (WO) dated Feb. 21, 2018 in International Application No. PCT/US2017/056129.
International Search Report and Written Opinion (WO) dated Jan. 17, 2018, in International Application No. PCT/US2017/045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.
International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jan. 5, 2017, in International Application No. PCT/US2016/058938.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The histroical Development ofMutaflor therapy," Ardeypharm GmbH, pp. 1-38 (1998) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Injlamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Itoh et al., "Characterization of clostridia isolated from faeces of limited flora mice and their effect on caecal size when associated with germ-free mice," *Laboratory Animals*, 19:111-118 (1985).
Itoh et al., "Intestinal bacteria antagonistic to *Clostridium difficile* in mice," *Laboratory Animals*, 21:20-25 (1987).
Ivanov et al., "Specific Microbiota Direct the Differentiation of IL-17-Producing T-Helper Cells in the Mucosa of the Small Intestine," *Cell Host & Microbe*, 4:337-349 (2008).
Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).

Janeway et al., "Adaptive Immunity to Infection," *Immunobiology*, 6th Edition, Chapter 10, pp. 414 (2005).
Janeway, Jr. et al., "Autoimmune responses are directed against self antigens," *Immunobiology: The Immune System in Health and Disease*, 5th Edition, pp. 1-4 (2001).
Jarvis et al., "National point prevalence of Clostridium difficile in US health care facility inpatients, 2008," *Am. J. Infect. Control*, 37:263-270 (2009).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," *Anaerobe*, 15(6):290-291 (2009).
Kageyama et al., "Emendation of genus *Collinsella* and proposal of *Collinsella stercoris* sp. nov. and *Collinsella intestinalis* sp. nov., " International Journal of Systematic and Evolutionary Microbiology, 50:1767-1774 (2000).
Kageyama et al., "Phylogenetic and phenotypic evidence for the transfer of Eubacterium aerofaciens to the genus *Collinsella* as *Collinsella aerofaciens* gen. nov., comb. nov., " International Journal of Systematic Bacteriology, 49:557-565 (1999).
Kakihana et al., "Fecal microbiota transplantation for patients with steriod-resistant acute graft-versus-host disease of the gut," Blood, 128(16):2083-2088 (2016)
Kamboj et al., "Relapse versus reinfection: surveillance of Clostridium difficile infection," *Clininfect Dis.*, 53(10):1003-1006 (2011).
Kang et al., "Microbiota Transfer Therapy alters gut ecosystem and improves gastrointestinal and autism symptoms: an open-label study," Microbiome, 5:10, 16 pages (2017).
Karas et al., "A review of mortality due to Clostridium difficile infection," *J Infect.*, 61(1):1-8 (2010).
Kassam et al., "Fecal transplant via retention enema for refractory or recurrent Clostridium difficile infection," *Arch Intern Med.*, 172(2):191-193 (2012).
Kelly et al., "Commensal gut bacteria: mechanisms of immune modulation," *TRENDS in Immunology*, 26(6):326-333 (2005).
Kelly et al., "Clostridium difficile—more difficult than ever," *N. Engl. J. Med.*, 359(18):1932-1940 (2008).
Kelly et al., "Clostridium difficile colitis," *N Engl. J Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantation for relapsing Clostridium difficile infection in 26 patients: methodology and results," *J Clin. Gastroenterol.*, 46(2):145-149 (2012).
Keynan et al., "The Role of Regulatory T Cells in Chronic and Acute Viral Infections," *Clinical Infectious Diseases*, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16.
Kharidia et al., "The Activity of a Small Lytic Peptide PTP-7 on *Staphylococcus aureus* Biofilms," *J Microbial.*, 49(4):663-668 (2011).
Khoruts el al., "Changes in the composition of the human fecal microbiome after bacteriotherapy for recurrent Clostridium difficile-associated diarrhea," *J Clin. Gastroenterol.*, 44(5):354-360 (2010).
Khomts et al., "Therapeutic transplantation of the distal gut microbiota," *Mucosa! Immunol.*, 4(1):4-7 (2011).
Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of

(56) References Cited

OTHER PUBLICATIONS

Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Klarenbeek et al., "Review of current classification for diverticular disease and a translation into clinical practice," Int. J. Colorectal Dis 27:207-214 (2012).
Kleiman et al., "Comparison of two coprological methods for the veterinary diagnosis of fasciolosis," Arquivo Brasileiro de Medicina Veterinaria e Zootccnica, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbial., 50:317-48 (1996).
Krogius-Kurikka et al., "Sequence analysis of percent G+C fraction libraries of human faecal bacterial DNA reveals a high number of Antinobacteria," BMC Microbiology, 9(68):1-13 (2009).
Kuijper et al. "Update of Clostridium difficile Infection due to PCR Ribotype 027 in Europe, 2008," Euro. Surveill., 13(31):Article 5 (2008).
Kuksal et al., "Formulation and In Vitro, In Vivo Evaluation of Extended- release Matrix Tablet of Zidovudine: Influence of Combination of Hydrophilic and Hydrophobic Matrix Formers," AAPS Pharm., 7(1):E1-E9 (2006).
Kunde et al., "Safety, Tolerability, and Clinical Response After Fecal Transplantation in Children and Young Adults With Ulcerative Colitis," JPNG, 56(6):597-601 (2013).
Kyne et al., "Association between antibody response to toxin A and protection against recurrent Clostridium difficile diarrhea," Lancet, 357(9251):189-93 (2001).
Kyne et al., "Asymptomatic carriage of Clostridium difficile and serum levels of IgG antibody against toxin A," N Engl J Med., 342(6):390-397 (2000).
Kyne et al., "Factors associated with prolonged symptoms and severe disease due to Clostridium difficile," Age and Ageing, 28(2):107-13 (1999).
Kysela et al., "Serial analysis of V6 ribosomal sequence tags (SARST-V6): a method for efficient, high-throughput analysis of microbial community composition," Environmental Microbiology, 7(3):356-364 (2005).
Labbe et al., "Clostridium difficile infections in a Canadian tertiary care hospital before and during a regional epidemic associated with the BI/NAP1/027 strain," Antimicrob Agents Chemother., 52(9):3180-7 (2008).
Lamontagne et al., "Impact of emergency colectomy on survival of patients with fulminant Clostridium difficile colitis during an epidemic caused by a hypervirulent strain," Ann. Surg., 245(2):267-272 (2007).
Larsen et al., "Gut Microbiota in Human Adults with Type 2 Diabetes Differs from Non-Diabetic Adults," PLoS ONE, 5(2): e9085-e9095 (2010).
Lau et al., "Bacteraemia caused by Anaerotruncus colihominisand emended description of the species," JClin Pathol, 59:748-752 (2006).
Lawson et al., "Anaerotruncus colihominis gen. nov., sp. nov., from human faeces," International Journal of Systematic and Evolutionary Microbiology, 54:413-417 (2004).
Lawson et al., "Anaerotruncus," Bergey's Manual of Systematics of Archae and Bacteria, pp. 1-4 (2009).
Lee et al., "Prioritizing candidate disease genes by network-based boosting of genome-wide association data," Genome Research, 21(1):1109-1121 (2011).
Lee et al., "The outcome and long-term follow-up of 94 patients with recurrent and refractory Clostridium difficile infection using single to multiple fecal microbiota transplantation vie retention enema," European Journal Clinical Microbiology Infect Dis., 33:1425-1428 (2014).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," Collegian, 22:445-451 (2015).
Leslie et al., "Trehalose and sucrose Protect Both Membranes and Proteins in Intact Bacteria during Drying," Applied and Environmental Microbiology, 61:3592-3597 (1995).
Lewis et al., "Stool form scale as a useful guide to intestinal transit time," Scand. J Gastroenterol., 32(9):920-924 (1997).
Ley et al., "Ecological and evolutionary forces shaping microbial diversity in the human intestine," Cell, 124:837-848 (2006).
Ley et al., "Evolution of mammals and their gut microbes," Science, 320(5883):1647-1651 (2008).
Ley et al., "Microbial ecology: human gut microbes associated with obesity," Nature, 444(7122):1022-3 (2006).
Ley et al., "Worlds within worlds: evolution of the vertebrate gut microbiota," Nat. Rev. Microbial., 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Loo et al., "A predominantly clonal multi institutional outbreak of Clostridium difficile-associated diarrhea with high morbidity and mortality," N Engl J Med, 353(23):2442-9 (2005).
Loo et al., "Host and pathogen factors for Clostridium difficile infection and colonization," N Engl J Med, 365(18):1693-703 (2011).
Louie et al., "Fidaxomicin versus vancomycin for Clostridium difficile infection," N Engl. J. Med., 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," FEMS Microbiology Letters, 294:1-8 (2009).
Lu, "Taboo transplant: How new poo defeats superbugs," Science News, 1:90-91 (2011).
Ludwig et al., "Taxonomic outline of the phylumFirmicutes, "Bergey's Manual of Systematic Bacteriology, 3:15-17 (2009).
Lund-Tonnesen et al., "Clostridium difficile-associated diarrhea treated with homologous faeces," Tidsskr Nor Lageforen, 118:1027-1030 (1998).
MacConnachie et al., "Faecal transplant for recurrent Clostridium difficile-associated diarrhoea: a UK case series," QJM, 102(11):781-784 (2009).
MacDonald et al., "Formation of Ursodeoxycholic Acid from Chenodeoxycholic Acid by a 7b -Hydroxysteroid Dehydrogenase-Elaborating Eubacterium aerofaciens Strain Cocultured with 7a-Hydroxysteroid Dehydrogenase-Elaborating Organisms," Applied and Environmental Microbiology, 44(5):1187-1195 (1982)
Macpherson et al., "Induction of Protective IgA by Intestinal Dendritic Cells Carrying Commensal Bacteria," Science, 303:1662-1665 (2004).
Madsen, "The use of probiotics in gastrointestinal disease," Can J Gastroenterol, 15(12):817-22 (2001).
Maizels et al., "Regulatory T cells in Infection," Advances in Immunology, Chapter 3, 112:73-136 (2011).
Manichanh et al., "Reshaping the gut microbiome with bacterial transplantation and antibiotic intake," Genome Research20:1411-1419 (2010).
Marchesi et al., "The normal intestinal microbiota," Curr. Opin. Infect. Dis., 20(5):508-513 (2007).
Martin, "Development and Delivery of a Treatment for Clostridium difficile," Bacteriotherapy, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process

(56) References Cited

OTHER PUBLICATIONS in order to target the colon: Interest of flow cytometry," European Journal of Pharmaceutical Sciences, 49:166-74 (2013).
Maslowski et al., "Diet, gut microbiota and immune responses," *Nat Immunol.*, 12(1):5-9(2011).
McDonald et al., "An Epidemic, Toxin Gene-Variant Strain of Clostridium difficile," *N Engl J Med.*, 353(23):12433-41 (2005).
McDonald et al., "Clostridium difficile Infection in Patients Discharged from US Short-stay Hospitals, 1996-2003" *Emerg. Infect. Dis*, 12(3):1409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999)
McFarland et al., "Renewed interest in a difficult disease: Clostridium difficile infections—epidemiology and current treatment strategies," *Curr Opin Gastroenterol.*, 25(1):24-35 (2008).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," *J Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *Anaerobe*, 15(6):281-284 (2009).
Moayyedi et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure Autism Now Foundation, pp. 1-7 (2005) <www.cureautismnow.org>.
Momose et al., "16S rRNA gene sequence-based analysis of clostridia related to conversion of germfree mice to the normal state," *Journal of Applied Microbiology*, 107:2088-2097 (2009).
Morris et al., "Clostridium difficile Colitis: An Increasingly Aggressive Iatrogenic Disease?" *Arch Surg.*, 137(10):1096-1100 (2002).
Mucosal immunity: homeostasis (WS-064): Chairpersons: Toshiaki Ohteki, Makoto Iwata, *International Immunology*, 22:Suppl 1 Pt. 3, 1-9 (2010).
Mullard, "Microbiology: The Inside Story," *Nature*, 453:578-580 (2008).
Murai et al., "Interleukin 10 acts on regulatory T cells to maintain expression of the transcription factor Foxp3 and suppressive function in mice with colitis," *Nat Immunol.*, pp. 1-20 (2009).
Mutaflor, "Brief Summary of Therapeutic Principles," Ardeypharm GmbH 0796 C- 58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988)
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneeskd*, 152(35):1927-32 (2008) (English abstract).
Niu et al., "Prevalence and Impact of Bacteriophages on the Presence of *Escherichia coli* O157:H7 in Feedlot Cattle and Their Environment," Applied and Environmental Microbiology, 75(5): 1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
O'Connor et al., "Clostridium difficile Infection Caused by the Epidemic BI/NAP1/027 Strain," *Gastroenterology*, 136(6):1913-1924 (2009).
Office Action dated Sep. 18, 2015, in European Patent Application No. 11 728 077.6.
O'Garra et al., "IL-10—producing and naturally occurring CD4+ Tregs: limiting collateral damage," *The Journal of Clinical Investigation*, 114:1372-1378 (2004).
O'Hara et al., "Functional modulation of human intestinal epithelial cell responses by Bifidobacterium infantis and Lactobacillus salivarms," *Immunology* 118:202-215 (2006).
Okada et al., "Effects of Fecal Microorganisms and Their Chloroform-Resistant Variants Derived from Mice, Rats, and Humans on Immunological and Physiological Characteristics of the Intestines ofExgermfree Mice," *Infection and Immunity*, 62(12):5442-5446 (1994).
Olson et al., "The Gut Microbiota Mediates the Anti-Seizure Effects of the Ketogenic Diet," Cell, 173:1728-1741 (2018) <https://linkinghub.elsevier.com/retrieve/pii/S0092867418305208>.
Ott et al., "Efficacy of Sterile Fecal Filtrate Transfer for Treating Patients With Clostridium difficile Infection," Gastroenterology, 152(4):799-811 (2017).
Paramsothy et al., "Gastroenterologist perceptions of faecal microbiota transplantation," *World J Gastroenterol*, 21(38): 10907-10914 (2015).
Paramsothy et al., "Multidonor intesive faecal microbiota transplantatin for active ulcerative colitis: a randomised placebo-controlled trial," The Lancet, published online, 11 pages (2017).
Paterson et al., "Putting back the bugs: Bacterial treatment relieves chronic diarrhoea," *Med J Aus*, 160:232-233 (1994)
Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 4l(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pepin et al., "Clostridium difficile-associated diarrhea in a region of Quebec from 1991 to 2003: a changing pattern of disease severity," *CMAJ*, 171(5):466-472 (2004).
Pepin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pepin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of Clostridium difficile infection: 'RePOOPulating'the gut," *Microbiome*, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.

(56) References Cited

OTHER PUBLICATIONS

Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), Remington: The Science and Practice of Pharmacy, Chapter 46, pp. 929-938 (2005).
Poster 064-03 presented at the 14th International Congress of Immunology, Aug. 22-27, 2010, in Kyoto (Atarashi et al., Regulation of colonic regulatroy T cells by *Colstridium* species).
Prakash et al., "Colon-targeted delivery of live bacterial cell biotherapeutics including microencapsulated live baterial cells," *Biologics: Targets & Therapy*, 2(3):355-378 (2008).
Prevention of Sudden Infant Death Syndrome, Healthtouch.com, Thomson MICROMEDEX, pp. 1-4, n.d., Web, 23 Nov. 2005.
Qiu el al., "*Faecalibacterium prausnitzii* upregulates regulatory T cells and anti-inflammatory cytokines in treating TNBS-induced colitis," *Journal of Crohn's and Colitis*, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of Clostridium difficile infection," Journal of Medical Microbiology, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11728077.6.
Response to Office Action filed Jan. 28, 2015, in European Patent Application No. 11728077.6.
Response to Office Action filed Nov. 18, 2015, in European Patent Application No. 11728077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," *Clin Gastroenterol Hepatol.*, 5(3):339-344 (2007)
Rohlke et al., "Fecal flora reconstitution for recurrent Clostridium difficile infection: results and methodology," *J Clin Gastroenterol.*, 44(8):567-570 (2010).
Rolfe et al., "Bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "Inducible Foxp3+ regulatory T-cell development by a commensal bacterium of the intestinal microbiota," *PNAS*, 107(27):12204-12209 (2010).
Round et al., "The gut microbiota shapes intestinal immune responses during health and disease," *Nat. Rev. Immunol.*, 9(5):313-323 (2009).

Rupnik et al., "Clostridium difficile infection: new developments in epidemiology and pathogenesis," *Nat. Rev. Microbial.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J Infect. Dis.*, 186(12):1781-1789 (2002).
Sanchez et al., "The Role of Natural Regulatory T cells in Infection," *Immunol Res.*, 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," *PNAS*, 105(43):16413-16414 (2008).
Schiller, "Review article," the therapy of constipation, Ailment Pharmacol. Ther., 15:749-763 (2001).
Schloss, "Introducing mothur: Open-Source, Platform-Independent, Community-Supported Software for Describing and Comparing Microbial Communities," *Appl. Environ. Microbial.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983)
Schwan et al., "Relapsing *Clostridium difficile* Enterocolitis Cured by Rectal Infusion of Normal Faeces," *Scand. J Infect. Dis.*, 16(2):211-215 (1984).
Seeff et al., "How many endoscopies are performed for colorectal cancer screening? Results from CDC's survey of endoscopic capacity," *Gastroenterology*, 127:1610-1611 (2004).
Sekirov et al., "Gut microbiota in health and disease," *Physiol. Rev.*, 90(3):859-904 (2010).
Sell et al., "Bacteriophage and Bacteriocin Typing Scheme for Clostridium difficile," Journal of Clinical Microbiology, 17(6):1148-1152 (1983).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shannon et al., "The Mathematical Theory of Communication," *The University of Illinois Press, Urbana* pp. 117 (1949).
Shi et al., "Fecal Microbiota Transplantation for Ulcerative Colitis: A Systematic Review and Meta-Analysis," PLOS One, 1-18 (2016).
Shim et al., "Primary symptomless colonisation by *Clostridium difficile* and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gatroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," Gastroenterology, 145:946-953 (2013)
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Inflamm. Bowel Dis.*, pp. 1-7 (2009).
Sullivan et al., "Effect of supplement with lactic-acid producing bacteria on fatigue and physical activity inpatients with chronic fatigue syndrome," Nutritional Journal, 8(4):1-6 (2009).

(56) References Cited

OTHER PUBLICATIONS

Sunil et al., "Design and evaluation of lomoxicam bilayered tablets for biphasic release," Brazilian Journal of Pharmaceutical Sciences, 48(4):609-19 (2012).

Surawicz et al., "Treatment of refractory and recurrent Clostridium difficile infection," *Nat. Rev. Gastroenterol. Hepatol.*, 8(6):330-339 (2011).

Surawicz, "Reining in Recurrent Clostridium difficile Infection—Who's at Risk?," *Gastroenterology*, 136:1152-1154 (2009).

Sutherland et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).

Takaishi et al., "Imbalance in intestinal microflora constitution could be involved in the pathogenesis of inflammatory bowel disease," *J. Med. Microbial.*, 298:463-472 (2008).

Takeda et al., "Serum Haloperidol Levels of Schizophrenics Receiving Treatment for Tuberculosis," Clinical Neuropharmacology, 9(4):386-397 (1986).

Tan et al., "Predictors of acute diverticulitis severity: A systematic review," *International Journal of Surgery* 26:43-52 (2016).

Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).

Tanoue et al., "Immune response to gut microbiota-commensals and pathogens," Gut Microbes, 1(4):224-233 (2010).

Taras et al., "Reclassification of Eubacterium formicigenerans Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).

Teasley et al., "Prospective randomised trial of metronidazole versus vancomycin for Clostridium-difficile-associated diarrhoea and colitis," *The Lancet*, 2(8358):1043-1046 (1983)

Tian et al., "Freeze-dried, Capsulized Fecal Microbiota Transplantation for Relapsing Clostridium difficile Infection," Journal of Clinical Gastroenterology, 49(6):537-538 (2015).

Tilg et al., "Gut microbiome, obesity, and metabolic dysfunction," *J Clin. Invest.*, 121(6):2126-2132 (2011).

Tursi et al., "Randomised clinical trial: mesalazine and/or probiotics in maintaining remission of symptomatic uncomplicated diverticular disease—a double-blind, randomized, placebo-controlled study," *Alimentary Pharmacology and Therapeutics* 38:741-751 (2013).

Tvede et al., "Bacteriotherapy for chronic relapsing Clostridium difficile diarrhea in six patients," *The Lancet*, 1:1156-1160 (1989).

Van Andel et al., "Interleukin-12 Has a Role in Mediating Resistance of Murine Strains to Tyzzer's Disease," Infect. Immun., 66(10):4942-4946 (1998).

Van der Waaij et al., "Direct Flow Cytometry of Anaerobic Bacteria in Human Feces," *Cytometry*, 16:270-279 (1994).

Van Immerseel et al., "Butyric acid-producing anaerobic bacteria as a novel probiotic treatment approach for inflammatory bowel disease," *Journal of Medical Microbiology*, 59:141-143 (2010).

Van Nood et al., "Struggling with Recurrent Clostridium difficile Infections: Is Donor Faeces the Solution?," *Euro Surveill.*, 14(34):1-6 (2009).

Van Nood, "Duodenal infusion of donor feces for recurrent Clostridium difficile," *New England Journal of Medicine*, 368(5):407-415 (2013).

Vaughn et al., "Novel treatment options for ulcerative colitis," *Future Science*, 1-20 (2013).

Veldhuyzen van Zanten et al., "Drug Treatment of Functional Dyspepsia: A Systematic Analysis of Trial Methodology with Recommendations for Design of Future Trials," *Am. J Gastroenterol.*, 91(4):660-673 (1996).

Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).

Venugopal et al., "Fidaxomicin: A Novel Macrocyclic Antibiotic Approved for Treatment of Clostridium difficile Infection," *Clin Infect Dis*, 54(4):568-74 (2012).

Vrieze et al., "The environment within: how gut microbiota may influence metabolism and body composition," *Diabetologia*, 53(4):606-613 (2010).

Vulevic et al., "Modulation of the fecal microflora profile and immune function by a novel trans-galactooligosaccharide mixture (B-GOS) in healthy elderly volunteers," Am J Clin Nutr, 88:1438-46 (2008).

Wachsmann et al., "Characterization of an Orotic Acid Fermenting Bacterium, *Zymobacterium oroticum*, nov. gen., nov. spec.," *Journal of Bacteriology*, 68(4):400-404 (1954).

Walter et al., "Host-microbial symbiosis in the vertebrate gastrointestinal tract and the Lactobacillus reuteri paradigm," *PNAS USA*, 108(Suppl 1):4645-4652 (2011).

Warny et al., "Toxin production by an emerging strain of Clostridium difficile associated with outbreaks of severe disease in North America and Europe," *Lancet*, 366(9491):1079-84 (2005).

Warren et al., "*Clostridium aldenense* sp. nov. and *Clostridium citroniae* sp. nov. Isolated from Human Clinical Infections," *Journal of Clinical Microbiology*, 44(7):2416-2422 (2006).

Wasfy et al., "Comparison of Preservation Media for Storage of Stool Samples," Journal of Clinical Microbiology, 33(8):2176-2178 (1995).

Weingarden et al., "Dynamic changes in short- and long-term bacterial composition following fecal microbiota transplantation for recurrent Clostridium difficile infection," Microbiome, 3(10), 8 pages (2015).

Weissman et al., "Stool Transplants: Ready for Prime Time?," Current Gastroenterology Reports, 14:313-316 (2012).

Wells et al., "Clostridia: Sporeforming Anaerobic Bacilli," *Medical Microbiology—NCBI Bookshelf*, 4th Edition, Chapter 18, pp. 1-20 (1996) <https://www.ncbi.nlm.nih.gov/books/NBK8219/?report=printable>.

Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).

Wettstein et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).

Wettstein et al., "Skewered diverticulum: another cause of abdominal pain," *Internal MedJ*, 31(8):495-496 (2001).

Wikoff et al., "Metabolomics analysis reveals large effects of gut microflora on mammalian blood metabolites," *PNAS*, 106(10):3698-3703 (2009).

Wilson et al., "Human Colonic Biota Studied by Ribosomal DNA Sequence Analysis," *Appl. Environ. Microbial.*, 62(7):2273-2278 (1996).

Yoon et al., "Treatment of Refractory/Recurrent C. difficile-associated Disease by Donated Stool Transplanted via Colonoscopy: A Case Series of 12 patients," *J Clin Gastroenterol.*, 44(8):562-566 (2010)

You et al., "Successful treatment of fulminant Clostridium difficile infection with fecal bacteriotherapy," *Ann. Intern. Med.*, 148(8):632-633 (2008).

Youngster et al., "Oral, Capsulized, Frozen Microbiota Transplantation for Relapsing Clostridium difficile Infection," *American Medical Association*, 312 (174) 1772-1778 (2014).

Yue et al., "Similarity Measure Based on Species Proportions," *Commun. Stat. Theor. Methods*, 34(11):2123-2131 (2005).

Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).

Zhang et al., "Influence of Microbiota on Intestinal Immune System in Ulcerative Colitis and Its Intervention," Frontiers in Immunology, 8(Article 1674):1-11 (2017).

Zhang et al., "Altered gut microbiome composition in children with refractory epilepsy after ketogenic diet," *Epilepsy Research* (2018) <https://doi.org/10.1016/j.eplepsyres.2018.06.15>.

(56) References Cited

OTHER PUBLICATIONS

Zhou et al., "Total fecal microbiota transplantation alleviates high-fat diet-induced steatohepatitis in mice via beneficial regulation of gut microbiota," *Scientific Reports (Nature)*, 7(1529):1-11 (2017).

Zilberberg et al., "Clostridium difficile Infections amoung Hospitalized Children," Emerg. Infect. Dis, 16(4):604-609 (2010).

Zilberberg et al., "Clostridium difficile-related Hospitalizations amoung US Adults," Emerg. Infect. Dis, 15(1):122-124 (2009).

Zilberberg et al., "Increase in Adult Clostridium difficile-related Hospitalization and Case-Fatality Rate," Emerg. Infect. Dis, 14(6):929-931 (2008).

Zilberberg et al., "Increase in Clostridium difficile-related Hospitalizations Amoung Infants in the United States, 2001-2005" Pediatr Infect Dis. J, 27(12):1111-1113 (2008).

Zoppi et al., "Oral Bacteriotherapy in Clinical Practice," Eur J. Pediatr, 139(1):18-21 (1982).

Zoppi et al., "The Intenstinal Ecosystem in Chronic Functional Constipation," ACTA Paediatr, 836-841 (1998).

Brandt et al., "An overview of fecal microbiota transplantation: techniques, indications, and outcomes," *Gastrointestinal Endoscopy*, 78:240-249 (2013).

Sampson et al., "Gut Microbiota Regulate Motor Deficits and Neuroinflammation in a Model of Parkinson's Disease," Cell, 167:1469-1480 (2016).

\* cited by examiner

COMPOSITIONS AND METHODS FOR TREATING PARKINSON'S DISEASE (PD) AND RELATED DISORDERS

CROSS-REFERENCE TO RELATED APPLICATIONS

This application is a national phase under 35 U.S.C. § 371 of International Application No. PCT/US2018/026080, filed on Apr. 4, 2018, which claims priority to U.S. Provisional Application No. 62/482,162, filed 5 Apr. 5, 2017, and U.S. Provisional Application No. 62/511,740, filed May 26, 2017. Each of these U.S. Provisional Applications are incorporated by reference herein in their entireties.

FIELD

The present disclosure relates to pharmaceutical compositions and methods suitable for treating Parkinson's disease (PD) and related disorders.

BACKGROUND

Mammals harbor diverse microbial species in their gastrointestinal (GI) tracts. Interactions between these microbes and between microbes and the host, e.g. the host immune system, shape a microbiota. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. An unbalanced microbiota (also called 'dysbiosis' or disrupted symbiosis) may lose its function and result in increased susceptibility to pathogens, altered metabolic profiles, or induction of proinflammatory signals that can lead to local or systemic inflammation or autoimmunity. Additionally, such a disrupted microbiota may be infected by incoming pathogen or pathogens, which can cause pain, diarrhea, gas, constipation among other symptoms. Hence, the intestinal microbiota plays a significant role in the pathogenesis of many disorders such as pathogenic infections of the gut.

Implantation or administration of human colonic microbiota into the bowel of a sick patient is called Fecal Microbiota Transplantation (FMT), also commonly known as fecal bacteriotherapy. FMT is believed to repopulate the gut with a diverse array of microbes that control key pathogens by creating an ecological environment inimical to their proliferation and survival. It represents a therapeutic protocol that allows a fast reconstitution of a normal compositional and functional gut microbial community.

FMT has been used to treat *Clostridium difficile* infection (CDI). FMT has also been suggested in treating other gut infective agents such as *E. coli* and Vancomycin resistant Enterococci (VRE). It entails infusions through a colonoscope, an enema or via a nasojejunal tube of human microbiota either in the form of homogenised stool, or cultured stool components such as Clostridia, to implant in the colon and thereby displace or eradicate pathogenic bacteria, e.g., *C. difficile*.

Parkinson's disease (PD) is a chronic progressive disorder of the nervous system that affects movement. PD develops as neurons in the substantia nigra region of the brain are lost, resulting in reduced availability of the neurotransmitter dopamine. Dopamine levels may also be decreased in the intestines. Nearly one million people in the US are living with PD. PD usually develops around age 60 and risks increase with age. Men are more likely to develop PD than woman. A family history of PD and ongoing exposure to herbicides and pesticides may put a person at increased risk.

PD causes stiffness or slow movements. PD can develop slowly and often times start with a slight tremor of the hand or development of soft or slurred speech. Patients also suffer from postural instability. Gastrointestinal symptoms include feelings of nausea or bloating, difficulty eliminating and constipation.

The severity of PD can be classified as mild, moderate, or advanced. In the mild stage of PD patients present with tremor, changes in facial expression, and possible slight movement symptoms. In the moderate stage patients may show movement symptoms on both sides of the body, including slowed movement, trouble balancing, and episodes when the feet feel "stuck" to the ground. In the advanced stage of PD walking becomes difficult, and hallucinations and delusions are prominent.

There currently exists no cure for PD, however, there are treatment options to manage symptoms. Some medications used to treat PD increase or substitute dopamine in a person's brain. Surgery can be used to regulate regions of the brain and improve symptoms. Although current therapies can alleviate some of the symptoms of PD, they have variable effectiveness, and are accompanied by unwanted side effects. Additionally, the patient's response to these therapies often decreases over time. Thus, there is an unmet medical need for additional drugs or therapies for more effective treatments for PD and related disorders that are easier to administer.

SUMMARY

The present disclosure provides compositions, methods, and dosing regimens for treating or preventing PD.

In one aspect, the present disclosure provides a method for treating PD in a subject in need thereof, where the method comprises administering to the subject a pharmaceutically active dose of a therapeutic composition comprising or derived from live non-pathogenic fecal bacteria or a sterile fecal filtrate. In one aspect, a sterile fecal filtrate originates from a donor stool. In another aspect, a sterile fecal filtrate originates from cultured microorganisms.

In another aspect, this disclosure provides use of a composition comprising live non-pathogenic fecal bacteria in the manufacture of a medication for the treatment of PD.

In one aspect, the present disclosure provides a method for treating PD in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily or at least once or twice weekly for at least three, eight, ten, or twenty consecutive weeks.

In one aspect, the present disclosure provides a method for treating PD in a subject in need thereof, where the method comprises administering orally to the subject a pharmaceutically active dose of a therapeutic composition comprising a liquid, frozen, lyophilized, or encapsulated sterile fecal filtrate, where the dose is administered at a dosing schedule of at least once or twice daily or at least once or twice weekly for at least three, eight, ten, or twenty consecutive weeks.

In one aspect, a method achieves a remission, cure, response, or resolution rate of PD of at least about 80%. In one aspect, the present disclosure provides a method which eliminates or reduces one or more PD symptoms selected from the group consisting of tremor, slowed movement (bradykinesia), rigid muscles, impaired posture and balance, loss of automatic movements, speech changes, and writing changes.

In an aspect, a fecal microbiota in a therapeutic composition comprises a donor's substantially entire and non-selected fecal microbiota, reconstituted fecal material, synthetic fecal material.

DETAILED DESCRIPTION

Unless defined otherwise herein, terms are to be understood according to conventional usage by those of ordinary skill in the relevant art.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

As used herein, "microbiota," and "flora" refer to a community of microbes that live in or on a subject's body, both sustainably and transiently, including eukaryotes, archaea, bacteria, and viruses (including bacterial viruses (i.e., phage)). A non-selected fecal microbiota refers to a community or mixture of fecal microbes derived from a donor's fecal sample without selection and substantially resembling microbial constituents and population structure found in such fecal sample.

As used herein, a "sterile fecal filtrate" or a "non-cellular fecal filtrate" refers to a liquid component of a fecal material, where the liquid component is free or substantially free of cell-based living organisms (e.g., bacteria, fungi, or their spores), but retains bacteriophages and non-cellular biological materials. Preferably, a non-cellular or sterile fecal filtrate is also free of viruses for eukaryotic host cells.

As used herein, "remission, cure, or resolution rate" refers to the percentage of patients that are cured or obtain remission or complete resolution of a condition in response to a given treatment. Remission, cure, or resolution of PD refers to complete cessation of one or more symptoms that a patient manifests prior to receiving a treatment described here. Such symptoms can include, but are not limited to, tremor, slowed movement (bradykinesia), rigid muscles, impaired posture and balance, loss of automatic movements, speech changes, and writing changes. Each of the foregoing symptoms are further explained below.

Tremor. A tremor, or shaking, usually begins in a limb, often a patient's hand or fingers. A patient may experience a back-and-forth rubbing of their thumb and forefinger, known as a pill-rolling tremor. One characteristic of Parkinson's disease is a tremor of a patient's hand when it is relaxed (at rest).

Slowed movement (bradykinesia). Over time, Parkinson's disease may reduce a patient's ability to move and slow a patient's movement, making simple tasks difficult and time-consuming. A patient's steps may become shorter when they walk, or they may find it difficult to get out of a chair. Also, a patient may drag their feet as them try to walk, making it difficult to move.

Rigid muscles. Muscle stiffness may occur in any part of a patient's body. The stiff muscles can limit a patient's range of motion and cause pain.

Impaired posture and balance. A patient's posture may become stooped, or the patient may have balance problems as a result of Parkinson's disease.

Loss of automatic movements. In Parkinson's disease, a patient may have a decreased ability to perform unconscious movements, including blinking, smiling or swinging their arms when they walk.

Speech changes. A patient may have speech problems as a result of Parkinson's disease. They may speak softly, quickly, slur or hesitate before talking. Their speech may be more of a monotone rather than with the usual inflections.

Writing changes. It may become hard to write, and a patient's writing may appear small.

As used herein, "response rate" refers to the percentage of patients that respond positively (e.g., reduced severity or frequency of one or more symptoms) to a given treatment.

As used herein, the staging of a PD patient is according to the Hoehn and Yahr Staging summarized in Table 1 (see also Hoehn M M, Yahr M D, Parkinsonism: onset, progression and mortality. *Neurology* 1967, 17:427-42)).

TABLE 1

Hoehn and Yahr Staging of Parkinson's Disease.

I. Stage One: (mild or early disease): Symptoms affect only one side of the body.
1. Signs and symptoms on one side only
2. Symptoms mild
3. Symptoms inconvenient but not disabling
4. Usually presents with tremor of one limb
5. Friends have noticed changes in posture, locomotion and facial expression
II. Stage Two: Both sides of the body are affected, but posture remains normal.
1. Symptoms are bilateral
2. Minimal disability
3. Posture and gait affected
III. Stage Three: (moderate disease): Both sides of the body are affected, and there is mild imbalance during standing or walking. However, the person remains independent.
1. Significant slowing of body movements
2. Early impairment of equilibrium on walking or standing
3. Generalized dysfunction that is moderately severe

TABLE 1-continued

Hoehn and Yahr Staging of Parkinson's Disease.

IV. Stage Four: (advanced disease): Both sides of the body are affected, and there is disabling instability while standing or walking. The person in this stage requires substantial help.
1. Severe symptoms
2. Can still walk to a limited extent
3. Rigidity and bradykinesia
4. No longer able to live alone
5. Tremor may be less than earlier stages V. Stage Five: (Severe) fully developed disease is present. The person is restricted to a bed or chair.
1. Cachectic stage
2. Invalidism complete
3. Cannot stand or walk
4. Requires constant nursing care As used herein, "Unified Parkinson Disease Rating Scale" or "UPDRS" refers to a rating tool to follow the longitudinal course of PD and represents the level or severity of PD symptoms (Table 2). UPDRS consists of a three-part test. It is made up of the 1) Mentation, Behavior, and Mood, 2) Activities of Daily Living (ADL) and 3) Motor sections. A total of 31 items are included in Parts I, II and III test. Each item receives a score ranging from 0 to 4 where 0 represents the absence of impairment and 4 represents the highest degree of impairment. The sum of Parts I, II and III at each study visit provides a Total UPDRS score. A total of 199 points are possible. 199 represents the worst (total) disability), 0—no disability. UPDRS is used for measuring the change from baseline in efficacy variables during a treatment described here.

TABLE 2

Unified Parkinson Disease Rating Scale (UPDRS) for characterizing severity of Parkinson's Disease.

I. Mentation, Behavior, Mood
Intellectual Impairment
0-none
1-mild (consistent forgetfulness with partial recollection of events with no other difficulties)
2-moderate memory loss with disorientation and moderate difficulty handling complex problems
3-severe memory loss with disorientation to time and often place, severe impairment with problems
4-severe memory loss with orientation only to person, unable to make judgments or solve problems
Thought Disorder
0-none
1-vivid dreaming
2-"benign" hallucination with insight retained
3-occasional to frequent hallucination or delusions without insight, could interfere with daily activities
4-persistent hallucination, delusions, or florid psychosis.
Depression
0-not present
1-periods of sadness or guilt greater than normal, never sustained for more than a few days or a week
2-sustained depression for >1 week
3-vegetative symptoms (insomnia, anorexia, abulia, weight loss)
4-vegetative symptoms with suicidality
Motivation/Initiative
0-normal
1-less of assertive, more passive
2-loss of initiative or disinterest in elective activities
3-loss of initiative or disinterest in day to say (routine) activities
4-withdrawn, complete loss of motivation
II. Activities of Daily Living
Speech
0-normal
1-mildly affected, no difficulty being understood
2-moderately affected, may be asked to repeat
3-severely affected, frequently asked to repeat
4-unintelligible most of time
Salivation
0-normal
1-slight but noticeable increase, may have nighttime drooling
2-moderately excessive saliva, hay minimal drooling
3-marked drooling TABLE 2-continued Unified Parkinson Disease Rating Scale (UPDRS) for characterizing severity of Parkinson's Disease.

Swallowing
0-normal
1-rare choking
2-occasional choking
3-requires soft food
4-requires NG tube or G-tube
Handwriting
0-normal
1-slightly small or slow
2-all words small but legible
3-severely affected, not all words legible
4-majority illegible
Cutting Food/Handing Utensils
0-normal
1-somewhat slow and clumsy but no help needed
2-can cut most foods, some help needed
3-food must be cut, but can feed self
4-needs to be fed
Dressing
0-normal
1-somewhat slow, no help needed
2-occasional help with buttons or arms in sleeves
3-considerable help required but can do something alone
4-helpless
Hygiene
0-normal
1-somewhat slow but no help needed
2-needs help with shower or bath or very slow in hygienic care
3-requires assistance for washing, brushing teeth, going to bathroom
4-helpless
Turning in Bed/Adjusting Bed Clothes
0-normal
1-somewhat slow no help needed
2-can turn alone or adjust sheets but with great difficulty
3-san initiate but not turn or adjust alone
4-helpless
Falling-Unrelated to Freezing
0-none
1-rare falls
2-occasional, less than one per day
3-average of once per day
4->1 per day
Freezing When Walking
0-normal
1-rare, may have start hesitation
2-occasional falls from freezing,
3-frequent freezing, occasional falls
4-frequent falls from freezin
Walking
0-normal
1-mild difficulty, day drag legs or decrease arm swing
2-moderate difficultly requires no assist
3-severe disturbance requires assistance
4-cannot walk at all even with assist
Tremor
0-absent
1-slight and infrequent, not bothersome to patient
2-moderate, bothersome to patient
3-severe, interfere with many activities
4-marked, interferes with many activities
Sensory Complaints Related to Parkinsonism
0-none
1-occasionally has numbness, tingling, and mild aching
2-frequent, but not distressing
3-frequent painful sensation
4-excruciating pain
III. Motor Exam
Speech
0-normal
1-slight loss of expression, diction,volume
2-monotone, slurred but understandable, mod. impaired
3-marked impairment, difficult to understand
4-unintelligible
Facial Expression
0-Normal
1-slight hypomymia, could be poker face
2-slight but definite abnormal diminution in expression TABLE 2-continued Unified Parkinson Disease Rating Scale (UPDRS) for
characterizing severity of Parkinson's Disease.

3-mod. hypomimia, lips parted some of time
4-masked or fixed face, lips parted ¼ of inch or more with complete loss of
expression
Tremor at Rest
Face
0-absent
1-slight and infrequent
2-mild and present most of time
3-moderate and present most of time
4-marked and present most of time
Right Upper Extremity (RUE)
0-absent
1-slight and infrequent
2-mild and present most of time
3-moderate and present most of time
4-marked and present most of time
LUE
0-absent
1-slight and infrequent
2-mild and present most of time
3-moderate and present most of time
4-marked and present most of time
RLE
0-absent
1-slight and infrequent
2-mild and present most of time
3-moderate and present most of time
4-marked and present most of time
LLE
0-absent
1-slight and infrequent
2-mild and present most of time
3-moderate and present most of time
4-marked and present most of time
Action or Postural Tremor
RUE
0-absent
1-slight, present with action
2-moderate, present with action
3-moderate present with action and posture holding
4-marked, interferes with feeding
LUE
0-absent
1-slight, present with action
2-moderate, present with action
3-moderate present with action and posture holding
4-marked, interferes with feeding
Rigidity
Neck
0-absent
1-slight or only with activation
2-mild/moderate
3-marked, full range of motion
4-severe
RUE
0-absent
1-slight or only with activation
2-mild/moderate
3-marked, full range of motion
4-severe
LUE
0-absent
1-slight or only with activation
2-mild/moderate
3-marked, full range of motion
4-severe
RLE
0-absent
1-slight or only with activation
2-mild/moderate
3-marked, full range of motion
4-severe
LLE
0-absent
1-slight or only with activation
2-mild/moderate
3-marked, full range of motion TABLE 2-continued Unified Parkinson Disease Rating Scale (UPDRS) for characterizing severity of Parkinson's Disease.

4-severe
Finger taps
Right
0-normal
1-mild slowing, and/or reduction in amp.
2-moderate impaired. Definite and early fatiguing, may have occasional arrests
3-severely impaired. Frequent hesitations and arrests.
4-can barely perform
Left
0-normal
1-mild slowing, and/or reduction in amp.
2-moderate impaired. Definite and early fatiguing, may have occasional arrests
3-severely impaired. Frequent hesitations and arrests.
4-can barely perform
Hand Movements (open and close hands in rapid succession)
Right
0-normal
1-mild slowing, and/or reduction in amp.
2-moderate impaired. Definite and early fatiguing, may have occasional arrests
3-severely impaired. Frequent hesitations and arrests.
4-can barely perform
Left
0-normal
1-mild slowing, and/or reduction in amp.
2-moderate impaired. Definite and early fatiguing, may have occasional arrests
3-severely impaired. Frequent hesitations and arrests.
4-can barely perform
Rapid Alternating Movements (pronate and supinate hands)
Right
0-normal
1-mild slowing, and/or reduction in amp.
2-moderate impaired. Definite and early fatiguing, may have occasional arrests
3-severely impaired. Frequent hesitations and arrests.
4-can barely perform
Left
0-normal
1-mild slowing, and/or reduction in amp.
2-moderate impaired. Definite and early fatiguing, may have occasional arrests
3-severely impaired. Frequent hesitations and arrests.
4-can barely perform
Leg Agility (tap heel on ground, amp should be 3 inches)
Right
0-normal
1-mild slowing, and/or reduction in amp.
2-moderate impaired. Definite and early fatiguing, may have occasional arrests
3-severely impaired. Frequent hesitations and arrests.
4-can barely perform
Left
0-normal
1-mild slowing, and/or reduction in amp.
2-moderate impaired. Definite and early fatiguing, may have occasional arrests
3-severely impaired. Frequent hesitations and arrests.
4-can barely perform
Arising From Chair (pt. arises with arms folded across chest)
0-normal
1-slow, may need more than one attempt
2-pushes self up from arms or seat
3-tends to fall back, may need multiple tries but can arise without assistance
4-unable to arise without help
Posture
0-normal erect
1-slightly stooped, could be normal for older person
2-definitely abnormal, mod. stooped, may lean to one side
3-severely stooped with kyphosis
4-marked flexion with extreme abnormality of posture
Gait
0-normal
1-walks slowly, may shuffle with short steps, no festination or propulsion
2-walks with difficult, little or no assistance, some festination. short steps or propulsion
3-severe disturbance, frequent assistance
4-cannot walk TABLE 2-continued Unified Parkinson Disease Rating Scale (UPDRS) for characterizing severity of Parkinson's Disease.

Postural Stability (retropulsion test)
0-normal
1-recovers unaided
2-would fall if not caught
3-falls spontaneously
4-unable to stand
Body Bradykinesia/Hypokinesia
0-none
1-minimal slowness, could be normal, deliberate character
2-mild slowness and poverty of movement, definitely abnormal, or dec. amp. of movement
3-moderate slowness, poverty, or small amplitude As used herein, a "symptomatic anti-Parkinsonian therapy" refers to a non-fecal microbiome based therapy. Examples of such therapy include any of bromocriptine, benztropine, levodopa, ropinirole, pramipexole, rotigotine, cabergoline, entacapone, tolcapone, amantidine and selegiline.

As used herein, "reducing the rate of progression of PD" means reducing the deterioration experienced by a PD patient, e.g. as quantified by UPDRS score, as compared to the deterioration experienced by a PD patient not receiving a treatment provided here over a period of time.

As used herein, "delaying the need for symptomatic anti-Parkinsonian therapy" means delaying the need for a symptomatic anti-Parkinsonian therapy for a PD patient who receives fecal microbiome based therapy, as compared to a patient not receiving fecal microbiome based therapy.

As used herein, "early signs of PD" refer to one or more of the followings:
a) a resting 4- to 8-Hz pill-rolling tremor of one hand;
b) tremor which is maximal at rest, diminishes during movement, and is absent during sleep;
c) rigidity and slowing of movement (bradycardia), decreased movement (hypokinesia), and difficulty in initiating movement (akinesia);
d) the face becoming masklike, with mouth open and diminished blinking, which may be confused with depression;
e) the posture becoming stooped;
f) difficulty in initiating walking; the gait becoming shuffling with short steps, and the arms being held flexed to the waist so as to not swing with the stride;
g) steps occasionally inadvertently quickening, and the patient occasionally breaking into a run to keep from falling (festination);
h) tendency to fall forward (propulsion) or backward (retropropulsion) when the center of gravity is displaced, resulting from loss of postural reflexes;
i) Speech becoming hypophonic, with a characteristic monotonous, stuttering dysarthria;
j) Hypokinesia and impaired control of distal musculature resulting in micrographia and increased difficulty with daily living activities;
k) infrequent blinking and lack of facial expression;
l) decreased movement;
m) impaired postural reflexes; and/or
n) characteristic gait abnormality.

As used herein, an "early stage PD patient" is a PD patient at Stage I or II of the Parkinson's Disease as defined by Hoehn and Yahr, and who does not require symptomatic anti-Parkinsonian therapy. Preferably such PD patient does not require symptomatic treatment for at least the next 9 months. An early stage PD patient may be identified as such by performing relevant testing.

As used herein, "eukaryotic" refers to belonging to a cell that contains a nucleus and membrane-bound organelles.

As used herein, "bacteria," "bacterium," and "archaea" refer to single-celled prokaryotes that lack membrane bound nuclei and lack organelles.

As used herein, "colony forming units" (cfu) refers to an estimate of the number of viable microorganism cells in a given sample.

As used herein, "viable" means possessing the ability to multiply.

As used herein, "fecal bacteria" refers to bacteria that can be found in fecal matter.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $$H = -\sum_{i=1}^{R} p_i \ln p_i$$

where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As used herein, an "intermittent dosing schedule" means that that a therapeutic composition is administered for a period of time followed by a period of time (a treatment period) where treatment with such therapeutic composition is withheld (a rest period). Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day.

As used herein, a "continuous dosing schedule" refers to a dosing schedule where a therapeutic composition is administered during a treatment period without a rest period. Throughout the treatment period of a continuous dosing schedule, a therapeutic composition can be administered, for example, weekly, daily, or every other day, or every third day. On a day when a therapeutic composition is administered, it can be administered in a single dose, or in multiple doses throughout the day.

As used herein, "dosing frequency" refers to the frequency of administering doses of a therapeutic composition in a given time. Dosing frequency can be indicated as the number of doses per a given time, for example, once per day, once a week, or once in two weeks.

As used herein, "dosing interval" refers to the amount of time that elapses between multiple doses being administered to a subject.

PD is a central nervous system degenerative disorder. It is also known as idiopathic parkinsonism, or idiopathic Parkinson's disease. The cause of the disease remains unknown, but it is manifested by an impairment in neurons in the substantia nigra of the brain, resulting in lack of production of dopamine, a neurotransmitter. The reduction in dopamine levels can cause movement impairments via irregular nerve firing in the brain. Major motor impairments associated with PD include tremor, rigidity, bradykinesia, and postural instability.

Current pharmaceutical treatments for Parkinson's disease focus on dopaminergic agents, which either mimic dopamine, or increase levels of dopamine in the body. The most common therapy is levodopa, which is a metabolic precursor of dopamine. However, long term levodopa therapy is often accompanied by dyskinesias, which are sudden, involuntary movements. Additionally, an "on-off" effect develops with long term levodopa therapy, wherein the patient experiences normal movement during "on" times, and reverts to PD-related motor impairment during "off" times. As levodopa therapy progresses, these side effects increase, and the "off" times last longer. Other dopaminergic agents, anticholinergics and/or amantadine also are used either alone, or in combination with levodopa therapy.

Surgical procedures such as deep brain stimulation have also been employed to alleviate symptoms of Parkinson's disease. Recent studies have shown that certain regions of the brain are hyperactive in PD and may be contributing to PD tremors, and cortical stimulation has been proposed to improve symptoms of PD in a mouse model and in humans Many chronic diseases and disorders of the GI tract have chronic infection/infestation as their underlying pathological conditions (e.g., PD). In one aspect, the present disclosure includes and relates to the use of a fecal microbiota, one or more microbial species therefrom, an active fragment or component therefrom for the treatment and/or prophylaxis of various disease states (e.g., PD) related to the presence of 'abnormal' microflora in the GI tract. An active fragment of a bacterium can be any active molecule isolated from such bacteria by any known method for preparing/identifying active fragments of bacteria and proteins secreted from bacteria. Such methods include but are not limited to the following: sonication, osmotic shock, detergent lysis, high pressure, transfer appropriate DNA to other organisms, such as bacteria, plant or animal that is then used as a feed additive as described previously. In one aspect, an active fragment or component of a bacterium is selected from the group consisting of a mycolate or a derivative thereof, a polysaccharide, a lipoglycan, a small peptide, a thiopeptide, a protein, a nucleic acid molecule, a metabolite, a cell wall component, or any combination thereof. In one aspect, an active fragment is a protein or a secretion. In another aspect, an active fragment is a secreted protein.

In one aspect, the present disclosure provides a method for treating PD in a subject in need thereof, where the method comprises administering to the subject a pharmaceutically active dose of a therapeutic composition comprising live non-pathogenic fecal bacteria and/or a sterile fecal filtrate. In another aspect, this disclosure provides use of a composition comprising live non-pathogenic fecal bacteria and/or a sterile fecal filtrate in the manufacture of a medication for the treatment of PD.

In one aspect, a therapeutic composition comprises an isolated or purified population of live non-pathogenic fecal bacteria. In one aspect, a therapeutic composition comprises a non-selected fecal microbiota. In another aspect, a therapeutic composition comprises a non-selected and substantially complete fecal microbiota. In another aspect, a therapeutic composition comprises a full-spectrum fecal microbiota. In one aspect, besides a fecal microbiome-based therapy, a method further comprises administering to a patient concurrently or sequentially a symptomatic anti-Parkinsonian therapy. In another aspect, besides a fecal microbiome-based therapy, a method further comprises administering to a patient concurrently or sequentially bromocriptine, benztropine, levodopa, ropinirole, pramipexole, rotigotine, cabergoline, entacapone, tolcapone, amantadine, selegiline or a combination thereof.

In one aspect, a fecal microbiome-based PD therapy described here is used in combination with, consecutively, concurrently, or sequentially with another treatment selected from the group consisting of levodopa (with or without carbidopa), dopamine agonists (DAs), inhibitors of enzymes that inactivate dopamine (MAO B inhibitors and COMT inhibitors), anticholinergics, amantadine, and estrogen. In a further aspect, a fecal microbiome-based therapy described here is used in combination with one or more drugs selected from the group consisting of levodopa, a monoamine oxidase B (MAO B) inhibitor (e.g., selegiline and rasagiline), dopamine agonists (e.g., bromocriptine, pramipexole, ropinirole, transdermal rotigotine, and apomorphine given by injection), catechol-O-methyl transferase (COMT) inhibitors (e.g., tolcapone and entacapone), an anticholinergic medication (e.g., trihexyphenidyl, benztropine, orphenadrine, procyclidine, and biperiden), amantadine.

In one aspect, the present disclosure provides a method which eliminates or reduces one or more PD symptoms selected from the group consisting of tremor, slowed movement (bradykinesia), rigid muscles, impaired posture and balance, loss of automatic movements, speech changes, and writing changes. In another aspect, the present disclosure provides a method which eliminates, improves, relieves, or reduces one or more early PD symptoms. In another aspect, a treatment method provided here can reduce, relieve, or control one or more non-motor PD symptoms, e.g., depression, sleep disorder, dementia, psychosis and hallucinations.

In a further aspect, a treatment method provided here can reduce, relieve, or control one or more PD primary motor symptoms selected from the group consisting of tremor, bradykinesia, rigidity, and postural instability. In another aspect, a treatment method provided here can reduce, relieve, or control one or more PD secondary motor symptoms selected from the group consisting of freezing of gait, micrographia (a shrinkage in handwriting), mask-like expression (a person's face may appear less expressive than usual), unwanted accelerations, stooped posture (a tendency to lean forward), dystonia, Impaired fine motor dexterity and motor coordination, impaired gross motor coordination, poverty of movement (decreased arm swing), akathisia, speech problems (such as softness of voice or slurred speech caused by lack of muscle control), difficulty swallowing, sexual dysfunction, cramping, and drooling and excess saliva resulting from reduced swallowing movements. In another aspect, a treatment method provided here can reduce, relieve, or control in a PD patient one or more conditions selected from the group consisting of Loss of sense of smell, constipation
REM behavior disorder (a sleep disorder)
Mood disorders
Orthostatic hypotension (low blood pressure when standing up).
Sleep disturbances
Constipation
Bladder problems
Sexual problems
Excessive saliva
Weight loss or gain
Vision and dental problems
Fatigue and loss of energy
Depression
Fear and anxiety
Skin problems
Cognitive issues, such as memory difficulties, slowed thinking, confusion and in some cases, dementia and
Medication side effects, such as impulsive behaviors.

In one aspect, a PD treatment described here comprises no, or is substantially free of, one or more side effects selected from the group consisting of nausea, sleepiness, dizziness, headache, vomiting, dry mouth, blurred vision, constipation, difficulty emptying the bladder, impaired sweating, and rapid heart rate, low blood pressure after standing up, confusion, hallucinations, delusions, agitation, swelling in the lower legs and feet, swelling of the ankles, dyskinesia, orange discoloration of the urine, and psychosis.

In one aspect, a patient treated here is pretreated with 7-10 days of oral broad-spectrum antimicrobial therapy. In one aspect, a single-agent antibiotic regimen is used. In another aspect, a multiple-agent antibiotic regimen is used. Exemplary antibiotic regimens include the following: (a) ciprofloxacin and metronidazole; (b) trimethoprim-sulfamethoxazole and metronidazole; (c) moxifloxacin, (d) amoxicillin/clavulanic acid. Further exemplary antibiotics include piperacillin/tazobactam, ampicillin/sulbactam, ticarcillin/clavulanic acid, imipenem, meropenem, tigecycline (when severe penicillin allergy is a concern). In another aspect, a multiple-drug regimen may consist of metronidazole and a third-generation cephalosporin or a fluoroquinolone, such as the following: Ceftriaxone, Cefotaxime, Ciprofloxacin, and Levofloxacin.

In one aspect, the present disclosure provides a method for treating PD in a subject in need thereof, where the method comprises administering to the subject a pharmaceutically active dose of a therapeutic composition comprising live non-pathogenic bacteria. In one aspect, the present disclosure provides a method for treating PD in a subject in need thereof, where the method comprises administering daily or weekly to the subject a pharmaceutically active dose of a therapeutic composition comprising live non-pathogenic fecal bacteria. In one aspect, a therapeutic composition is administered to an PD patient in need thereof at least once daily or at least once weekly for at least two consecutive days or weeks. In one aspect, a therapeutic composition is administered at least once daily or at least once weekly for at least 3, 4, 5, 6, 7, 8, 9, 10, 11, 12, 13, 14, or 15 consecutive days or weeks. In another aspect, a therapeutic composition is administered at least once daily or at least once weekly for at least 1, 2, 3, 4, 5, 6, 7, 8, 9, 10, 11, or 12 consecutive weeks. In one aspect, a therapeutic composition is administered at least once daily or at least once weekly for at most 4, 5, 6, 7, 8, 9, 10, 11, 12, 13, 14, 15, 16, 17, 18, 19, or 20 consecutive days or weeks. In another aspect, a therapeutic composition is administered at least once daily or at least once weekly for at most 1, 2, 3, 4, 5, 6, 7, 8, 9, 10, 11, or 12 consecutive weeks or months. In a further aspect, a therapeutic composition is administered at least once for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an PD patient in need thereof at least twice daily or at least twice weekly for at least two consecutive days or weeks. In one aspect, a therapeutic composition is administered at least twice daily or at least twice weekly for at least 3, 4, 5, 6, 7, 8, 9, 10, 11, 12, 13, 14, or 15 consecutive days or weeks. In another aspect, a therapeutic composition is administered at least twice daily or at least twice weekly for at least 1, 2, 3, 4, 5, 6, 7, 8, 9, 10, 11, or 12 consecutive weeks. In one aspect, a therapeutic composition is administered at least twice daily or at least twice weekly for at most 4, 5, 6, 7, 8, 9, 10, 11, 12, 13, 14, 15, 16, 17, 18, 19, or 20 consecutive days or weeks. In another aspect, a therapeutic composition is administered at least twice daily or at least twice weekly for at most 1, 2, 3, 4, 5, 6, 7, 8, 9, 10, 11, or 12 consecutive weeks or months. In a further aspect, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an PD patient in need thereof at least three times daily or at least three times weekly for at least two consecutive days or weeks. In one aspect, a therapeutic composition is administered at least three times daily or at least three times weekly for at least 3, 4, 5, 6, 7, 8, 9, 10, 11, 12, 13, 14, or 15 consecutive days or weeks. In another aspect, a therapeutic composition is administered at least three times daily or at least three times weekly for at least 1, 2, 3, 4, 5, 6, 7, 8, 9, 10, 11, or 12 consecutive weeks. In one aspect, a therapeutic composition is administered at least three times daily or at least three times weekly for at most 4, 5, 6, 7, 8, 9, 10, 11, 12, 13, 14, 15, 16, 17, 18, 19, or 20 consecutive days or weeks. In another aspect, a therapeutic composition is administered at least three times daily or at least three times weekly for at most 1, 2, 3, 4, 5, 6, 7, 8, 9, 10, 11, or 12 consecutive weeks or months. In a further aspect, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one aspect, the present disclosure provides a method for treating PD in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily or at least once or twice weekly for at least three consecutive days or weeks. In another aspect, a dose is administered at least once, twice, or three times daily or at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one aspect, the present disclosure provides a method for treating PD in a subject in need thereof, where the method comprises a first dosing schedule followed by a second dosing schedule. In one aspect, a first dosing schedule comprises a treatment or induction dose. In one aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In one aspect, a second dosing schedule lasts permanently, for a treated subject's entire life span, or an indefinite period of time. In one aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In one aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In one aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In one aspect, a subject being treated is a subject already with PD. Administration of a disclosed therapeutic composition to clinically, asymptomatic human subject who is genetically predisposed or prone to PD is also useful in preventing the onset of clinical symptoms of PD. A human subject genetically predisposed or prone to PD can be a human subject having a close family member or relative exhibiting or having suffered PD. In another aspect, a subject being treated is a subject in which PD is to be prevented. In another aspect, a subject being treated is predisposed or susceptible to PD. In another aspect, a subject being treated is a subject diagnosed as having PD. In one aspect, a subject being treated is a patient in need of PD treatment. In another aspect, a patient being treated is immunocompromised. In another aspect, a patient being treated has both PD and a gastrointestinal disorder (e.g., chronic constipation, IBD, IBS, or a *C. diff* infection).

In one aspect, a subject being treated has a stage I, stage II, stage III, stage IV, or stage V PD. In one aspect, a method described here is capable of improving a PD patient's condition so that the patient's PD staging is reclassified by at least one or two stages (e.g., from stage III to stage II or from stage III to stage I). In another aspect, a method described here is capable of preventing a PD patient's condition from worsening so that the patient's PD staging remains the same or deteriorates more slowly. In another aspect, a method described here is capable of reducing the rate of progression of PD in a subject. In a further aspect, a method described here is capable of delaying the need for symptomatic anti-Parkinsonian therapy in a subject. In one aspect, a patient is subject to a treatment described here after being diagnosed with one or more early signs of Parkinson's disease.

In one aspect, a subject being treated is a human patient. In one aspect, a patient is a male patient. In one aspect, a patient is a female patient. In one aspect, a patient is a premuature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

In one aspect, a method comprises administering a therapeutic composition orally, by enema, or via rectal suppository. In one aspect, a therapeutic composition administered herein is formulated as an enteric coated (and/or acid-resistant) capsule or microcapsule, or formulated as part of or administered together with a food, a food additive, a dairy-based product, a soy-based product or a derivative thereof, a jelly, flavored liquid, ice block, ice-cream, or a yogurt. In another aspect, a therapeutic composition administered herein is formulated as an acid-resistant enteric coated capsule. A therapeutic composition can be provided as a powder for sale in combination with a food or drink. A food or drink can be a dairy-based product or a soy-based product. In another aspect, a food or food supplement contains enteric-coated and/or acid-resistant microcapsules containing a therapeutic composition.

In an aspect, a therapeutic composition comprises a liquid culture. In another aspect, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In one aspect, a powder may be reconstituted to be infused via naso-duodenal infusion.

In another aspect, a therapeutic composition administered herein is in a liquid, frozen, freeze-dried, spray-dried, foam-dried, lyophilized, or powder form. In a further aspect, a therapeutic composition administered herein is formulated as a delayed or gradual enteric release form. In another aspect, a therapeutic composition administered herein comprises an excipient, a saline, a buffer, a buffering agent, or a fluid-glucose-cellobiose agar (RGCA) media. In another aspect, a therapeutic composition administered herein comprises a cryoprotectant. In one aspect, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In one aspect, a therapeutic composition administered herein further comprises an acid suppressant, an antacid, an H2 antagonist, a proton pump inhibitor or a combination thereof. In one aspect, a therapeutic composition administered herein substantially free of non-living matter. In another aspect, a therapeutic composition administered herein substantially free of acellular material selected from the group consisting of residual fiber, DNA, viral coat material, and non-viable material.

In one aspect, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one aspect, a method further comprises pretreating a subject with an antibiotic composition prior to administering a therapeutic bacterial or microbiota composition. In one aspect, an antibiotic composition administered herein comprises an antibiotic selected from the group consisting of rifabutin, clarithromycin, clofazimine, vancomycin, rifampicin, nitroimidazole, chloramphenicol, and a combination thereof. In another aspect, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a therapeutic bacterial or microbiota composition.

In one aspect, a method achieves a remission, cure, response, or resolution rate of PD of at least about 10%, 15%, 20%, 25%, 30%, 35%, 40%, 45%, 50%, 55%, 60%, 65%, 70%, 75%, 80%, 85%, 90%, 95%, 97%, or 99%. In one aspect, a treatment method achieves a reduction of UPDRS score after 4, 8, or 12 weeks of treatment by more than 2, 3, 4, 5, 6, 7, 8, 9, 10, or 11. In another aspect, a treatment method achieves a reduction of UPDRS score after 4, 8, or 12 weeks of treatment by more than 2, 3, 4, 5, 6, 7, 8, 9, 10, or 11 in at least 10%, 20%, 30%, 50%, 60%, 70%, 80%, or 90% patients in a patient population. In one aspect, a treatment method achieves at least 10%, 20%, 30%, 50%, 60%, 70%, 80%, or 90% reduction of UPDRS score after 4, 8, or 12 weeks of treatment compared to baseline (e.g., immediately prior to treatment). In one aspect, a treatment method achieves at least 10%, 20%, 30%, 50%, 60%, 70%, 80%, or 90% reduction of UPDRS score in at least 10%, 20%, 30%, 50%, 60%, 70%, 80%, or 90% patients after 4, 8, or 12 weeks of treatment compared to baseline (e.g., immediately prior to treatment). Though UPDRS is used as an example for characterizing and quantifying PD severity, similar or comparable systems (e.g., MDS-UPDRS) can be used as well. Every instance in this application where UPDRS is mentioned, another similar scale or system can be used in lieu of UPDRS. Such alternative systems include, e.g., UPDRS disability score (UDS) (Martinez-Martin et al., *Neurologia*. 2000 November; 15(9):382-7). In another aspect, an UPDRS score reduction mentioned herein is a reduction of the total UPDRS score. In another aspect, an UPDRS score reduction mentioned herein refers to a reduction in any one or two of the subscores for 1) Mentation, Behavior, and Mood, 2) Activities of Daily Living (ADL) and 3) Motor sections.

In one aspect, a treatment method described here is capable of achieving a rapid onset of PD symptom improvement. In another aspect, a patient's PD symptom improves after one week of five or fewer fecal microbiome infusions via colonoscopic delivery or enema. In another aspect, after one treatment course described herein, a PD patient experience symptom improvement within 1, 2, 3, 4, 5, 6, 7, 8, 9, 10, 11, 12, 13, 14, or 15 weeks of initiating the treatment.

In another aspect, a PD patient is subject to a fecal microbe-based therapy which includes an induction phase of intensive dosing of fecal microbes followed by a maintenance phase of less intensive dosing. In one aspect, an induction phase comprises fresh fecal microbiome infusions via colonoscopic delivery or enema. In one aspect, an induction phase comprises 5 to 10 fresh fecal microbiome infusions via colonoscopic delivery or enema across 1 to 2 weeks. In another phase, an induction phase comprises ingesting acid-resistant/delayed release capsules containing lyophilized donor-derived, non-selected fecal microbiota. In one aspect, a maintenance phase comprises ingesting capsules containing lyophilized donor-derived, non-selected fecal microbiota. In a further aspect, a maintenance phase comprises daily intake of 6 or more, 4 or more, or 2 or more capsules where each capsule comprises about $10^{10}$ to $10^{13}$ total cell count. In a further aspect, a maintenance phase comprises intake of 6 or more, 4 or more, or 2 or more capsules every other day where each capsule comprises about $10^{10}$ to $10^{13}$ total cell count.

In one aspect, every about 200 mg of a pharmaceutical composition comprises a pharmacologically active dose. In one aspect, every about 75, 100, 125, 150, 175, 200, 250, 300, 350, 400, 450, 500, 750, 1000, 1500, or 2000 mg of a pharmaceutical composition comprises a pharmacologically active dose.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$, $10^{14}$, or $10^{15}$ cfu. In another aspect, a pharmaceutically active therapeutic effective dose comprises at most about $10^5$, $10^6$, $10^7$, $10^8$, $10^9$, $10^{10}$, $10^{11}$, $10^{12}$, $10^{13}$, $10^{14}$, or $10^{15}$ cfu cfu. In a further aspect, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In one aspect, a pharmaceutically active or therapeutic effective dose comprises at least about $10^5$, $10^6$, $10^7$, $10^8$, $10^9$, $10^{10}$, $10^{11}$, $10^{12}$, $10^{13}$, $10^{14}$, or $10^{15}$ cells or spores. In another aspect, a pharmaceutically active or therapeutic effective dose comprises at most about $10^5$, $10^6$, $10^7$, $10^8$, $10^9$, $10^{10}$, $10^{11}$, $10^{12}$, $10^{13}$, $10^{14}$, or $10^{15}$ total cells or spores. In a further aspect, a pharmacologically active or therapeutic effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutic effective dose cell count is directed to live cells. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter. In an aspect, a pharmaceutically active or therapeutic effective dose comprises between $10^{10}$ and $10^{12}$ cells. In another aspect, a pharmaceutically active or therapeutic effective dose comprises between $10^{10}$ and $10^{12}$ cells per capsule.

In one aspect, a therapeutic composition administered herein comprises fecal bacteria. In one aspect, a therapeutic composition administered herein comprises one or more, two or more, three or more, four or more, or five or more isolated, purified, or cultured microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea*, and *Monilia*.

In one aspect, a therapeutic composition administered herein comprises at least one, at least two, at least three, at least four, at least five, at least six, or at least seven fecal microorganisms selected from the group consisting of a *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus,* -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

In one aspect, a therapeutic composition administered herein comprises no viable *Bacteroides, Fusobacterium, Propionibacterium, Lactobacillus, Ruminococcus, Escherichia coli, Gemmiger, Desulfomonas, Peptostreptococcus, Bifidobacterium, Monilia*, or any combination thereof. In another aspect, a therapeutic composition administered herein comprises no viable *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum,*

*Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale Coprococcus comes, Pseudollavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus*, -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, or a combination thereof.

In one aspect, a therapeutic composition administered herein comprises a fecal microbiota. In another aspect, the preparation of a fecal microbiota used herein involves a treatment selected from the group consisting of ethanol treatment, detergent treatment, heat treatment, irradiation, and sonication. In another aspect, the preparation of a fecal microbiota used herein involves no treatment selected from the group consisting of ethanol treatment, detergent treatment, heat treatment, irradiation, and sonication. In one aspect, the preparation of a fecal microbiota used herein involves a separation step selected from the group consisting of density gradients, filtration (e.g., sieves, nylon mesh), and chromatography. In another aspect, the preparation of a fecal microbiota used herein involves no separation step selected from the group consisting of density gradients, filtration (e.g., sieves, nylon mesh), and chromatography. In another aspect, a fecal microbiota used herein comprises a donor's entire fecal microbiota. In another aspect, a therapeutic composition administered herein comprises a fecal microbiota substantially free of eukaryotic cells from the fecal microbiota's donor.

In another aspect, a therapeutic composition administered herein comprises a fecal microbiota further supplemented, spiked, or enhanced with a fecal microorganism. In one aspect, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Baccillus*, or a combination thereof. In another aspect, a therapeutic composition administered herein comprises a fecal microbiota further supplemented, spiked, or enhanced with a species of *Veillonellaceae, Firmicutes, Gammaproteobacteria, Bacteroidetes*, or a combination thereof. In another aspect, a therapeutic composition administered herein comprises a fecal microbiota further supplemented with fecal bacterial spores. In one aspect, fecal bacterial spores are *Clostridium* spores, *Bacillus* spores, or both.

In an aspect, a therapeutic composition comprises a fecal microbiota from a subject selected from the group consisting of a human, a bovine, a dairy calf, a ruminant, an ovine, a caprine, or a cervine. In another aspect, a therapeutic composition can be administered to a subject selected from the group consisting of a human, a bovine, a dairy calf, a ruminant, an ovine, a caprine, or a cervine. In an aspect, a therapeutic composition is substantially or nearly odourless.

In an aspect, a therapeutic composition provided or administered herein comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a therapeutic composition comprises a preparation of flora in proportional content that resembles a normal healthy human fecal flora.

In a further aspect, a therapeutic composition comprises fecal bacteria from at least 1, 2, 3, 4, 5, 6, 7, 8, 9, or 10 different families. In an aspect, a therapeutic composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a therapeutic composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a therapeutic composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.33 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, 0.002 mm, 0.1 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one aspect, "biological material" refers to the living material, e.g., the microbes, eukaryotic cells, and viruses, which are present in the colon of a normal healthy human. In an aspect, a therapeutic composition provided or administered herein comprises an extract of human feces where the composition is substantially odorless. In an aspect, a therapeutic composition provided or administered herein comprises fecal material or a fecal floral preparation in a lyophilized, crude, semi-purified or purified formulation.

In an aspect, a fecal microbiota in a therapeutic composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, a fecal microbiota in a therapeutic composition comprises a donor's substantially entire or non-selected fecal microbiota, reconstituted fecal material, or synthetic fecal material. In another aspect, the fecal microbiota in a therapeutic composition comprises no antibiotic resistant population. In another aspect, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a therapeutic composition used herein is derived from disease-screened fresh homologous feces or equivalent freeze-dried and reconstituted feces. In an aspect, a fresh homologous feces does not include an antibiotic resistant population. In another aspect, a fecal microbiota in a therapeutic composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea,* and *Ruminococcus*.

In an aspect, a therapeutic composition used in a treatment disclosed herein comprises a sterile fecal filtrate or a non-cellular fecal filtrate. In one aspect, a sterile fecal filtrate originates from a donor stool. In another aspect, a sterile fecal filtrate originates from cultured microorganisms. In another aspect, a sterile fecal filtrate comprises a non-cellular non-particulate fecal component. In one aspect, a sterile fecal filtrate is made as described in WO2014/078911, published May 30, 2014. In another aspect, a sterile fecal filtrate is made as described in Ott et al., *Gastroenterology* 152:799-911(2017).

In one aspect, a fecal filtrate comprises secreted, execreted or otherwise liquid components or a microbiota, e.g., biologically active molecules (BAMs), which can be antibiotics or anti-inflammatories, are preserved, retained or reconstituted in a flora extract.

In one aspect, an exemplary therapeutic composition comprises starting material from a donor from a defined donor pool, where this donor contributes a stool that is centrifuged, then filtered with very high-level filtration using e.g., either metal sieving or Millipore filters, or equivalent, to ultimately permit only cells of bacterial origin to remain, e.g., often less than about 5 micrometres diameter. After the initial centrifugation, the solid material is separated from the liquid, and the solid is then filtered in progressively reducing size filters and tangential filters, e.g., using a Millipore filtration, and optionally, also comprising use of nano-membrane filtering. The filtering can also be done by sieves as described in WO 2012/122478, but in contrast using sieves that are smaller than 0.0120 mm, down to about 0.0110 mm, which ultimately result in having only bacterial cells present.

The supernatant separated during centrifugation is now taken and filtered progressively in a filtering, e.g., a Millipore filtering or equivalent systems, to end up with liquid which is finely filtered through an about 0.22 micron filter. This removes all particulate matter including all living matter, including bacteria and viruses. The product then is sterile, but the aim is to remove the bacteria but to keep their secretions, especially antimicrobial bacteriocins, bacteria-derived cytokine-like products and all accompanying Biologically Active Molecules (BAMs), including: thuricin (which is secreted by bacilli in donor stools), bacteriocins (including colicin, troudulixine or putaindicine, or microcin or subtilosin A), lanbiotics (including nisin, subtilin, epidermin, mutacin, mersacidin, actagardine, cinnamycin), lacticins and other antimicrobial or anti-inflammatory compounds.

In one aspect, a therapeutic composition used here comprises a reconstituted fecal flora consisting essentially of a combination of a purified fecal microbiota and a non-cellular fecal filtrate. In another aspect, a therapeutic composition used here comprises a purified fecal microbiota supplemented with one or more non-cellular non-particulate fecal components. In one aspect, a therapeutic composition used here comprises one or more non-cellular non-particulate fecal components. In one aspect, one or more non-cellular non-particulate fecal components comprise synthetic molecules, biologically active molecules produced by a fecal microorganism, or both. In another aspect, one or more non-cellular non-particulate fecal components comprise biologically active proteins or peptides, micronutrients, fats, sugars, small carbohydrates, trace elements, mineral salts, ash, mucous, amino acids, nutrients, vitamins, minerals, or any combination thereof. In one aspect, one or more non-cellular non-particulate fecal components comprise one or more biologically active molecules selected from the group consisting of bacteriocin, lanbiotic, and lacticin. In another aspect, one or more non-cellular non-particulate fecal components comprise one or more bacteriocins selected from the group consisting of colicin, troudulixine, putaindicine, microcin, and subtilosin A. In one aspect, one or more non-cellular non-particulate fecal components comprise one or more lanbiotics selected from the group consisting of thuricin, nisin, subtilin, epidermin, mutacin, mersacidin, actagardine, and cinnamycin. In another aspect, one or more non-cellular non-particulate fecal components comprise an anti-spore compound, an antimicrobial compound, an anti-inflammatory compound, or any combination thereof. In a further aspect, one or more non-cellular non-particulate fecal components comprise an interleukin, a cytokine, a leukotriene, an eicosanoid, or any combination thereof.

In another aspect, a treatment method provided here comprises the use of both fecal bacterial cells, e.g., a partial or a complete representation of the human GI microbiota, and an isolated, processed, filtered, concentrated, reconstituted and/or artificial liquid component (e.g., fecal filtrate) of the flora (the microbiota) which comprises, among others ingredients, bacterial secretory products such as e.g., bacteriocins (proteinaceous toxins produced by bacteria, including colicin, troudulixine or putaindicine, or microcin or subtilosin A), lanbiotics (a class of peptide antibiotics that contain a characteristic polycyclic thioether amino acid lanthionine or methyllanthionine, and unsaturated amino acids dehydroalanine and 2-aminoisobutyric acid; which include thuricin (which is secreted by bacilli in donor stools), nisin, subtilin, epidermin, mutacin, mersacidin, actagardine, cinnamycin), a lacticin (a family of pore-forming peptidic toxins) and other antimicrobial or anti-inflammatory compounds and/or additional biologically active molecules (BAMs) produced by bacteria or other microorganisms of the microbiota, and/or which are found in the "liquid component" of a microbiota.

In one aspect, a fecal bacteria-based therapeutic composition is used concurrently with a fecal non-cellular filtrate-based therapeutic composition. In another aspect, a patient is treated with a first fecal non-cellular filtrate-based therapeutic composition before being given a second fecal bacteria-based therapeutic composition, or vice versa. In a further aspect, a treatment method comprises three steps: first, antibiotic pre-treatment to non-selectively remove infectious pathogen(s); second, a fecal non-cellular filtrate-based treatment step to further suppress selected infectious pathogen(s); and third, giving the patient a fecal bacteria-based therapeutic composition to re-establish a functional intestinal microbiome.

In an aspect, a therapeutic composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a therapeutic composition.

In an aspect, a therapeutic composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of PD. In another aspect, a treatment method also effects a change of flora. The change of flora is preferably as "near-complete" as possible and the flora is replaced by viable organisms which will crowd out any remaining, original flora. Typically the change in enteric flora comprises introduction of an array of predetermined flora into the gastrointestinal system, and thus in a preferred form the method of treatment comprises substantially or completely displacing pathogenic enteric flora in patients requiring such treatment.

In another aspect, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a therapeutic composition may contain auxiliary substances such as wetting or emulsifying agents, stabilizing or pH buffering agents. In an aspect, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a therapeutic composition contains about 2%-70%, 5%-60%, 10%-50%, 15%-40%, 20%-30%, 25%-60%, 30%-60%, or 35%-60% of active ingredient.

In an aspect, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu or total cell count). A therapeutic composition used herein can be flavored.

In an aspect, a therapeutic composition can be a tablet or a pill. In one aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a therapeutic composition can be a drench. In one aspect, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a therapeutic composition comprises non-pathogenic spores of one or more, two or more, three or more, or four or more *Clostridium* species selected from the group consisting of *Clostridium absonum*, *Clostridium argentinense*, *Clostridium baratii*, *Clostridium botulinum*, *Clostridium cadaveris*, *Clostridium carnis*, *Clostridium celatum*, *Clostridium chauvoei*, *Clostridium clostridioforme*, *Clostridium cochlearium*, *Clostridium fallax*, *Clostridium felsineum*, *Clostridium ghonii*, *Clostridium glycolicum*, *Clostridium haemolyticum*, *Clostridium hastiforme*, *Clostridium histolyticum*, *Clostridium indolis*, *Clostridium irregulare*, *Clostridium limosum*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium sardiniense*, *Clostridium sartagoforme*, *Clostridium scindens*, *Clostridium septicum*, *Clostridium sordellii*, *Clostridium sphenoides*, *Clostridium spiroforme*, *Clostridium sporogenes*, *Clostridium subterminale*, *Clostridium symbiosum*, *Clostridium tertium*, *Clostridium tetani*, *Clostridium welchii*, and *Clostridium villosum*.

In an aspect, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella*, *Coprococcus*, *Dorea*, *Eubacterium*, and *Ruminococcus*. In another aspect, a therapeutic composition comprises a plurality of purified, isolated, or cultured viable non-pathogenic microorganisms from one or more genera selected from the group consisting of *Clostridium*, *Collinsella*, *Coprococcus*, *Dorea*, *Eubacterium*, and *Ruminococcus*.

In an aspect, a therapeutic composition comprises two or more genera selected from the group consisting of *Collinsella*, *Coprococcus*, *Dorea*, *Eubacterium*, and *Ruminococcus*. In another aspect, a therapeutic composition comprises two or more genera selected from the group consisting of *Coprococcus*, *Dorea*, *Eubacterium*, and *Ruminococcus*. In a further aspect, a therapeutic composition comprises one or more, two or more, three or more, four or more, or five or more species selected from the group consisting of *Coprococcus catus*, *Coprococcus comes*, *Dorea longicatena*, *Eubacterium eligens*, *Eubacterium hadrum*, *Eubacterium hallii*, *Eubacterium rectale*, and *Ruminococcus torques*.

In one aspect, a therapeutic composition comprises at least about $10^5$, $10^6$, $10^7$, $10^8$, $10^9$, $10^{10}$, $10^{11}$, $10^{12}$, or $10^{13}$ cfu or total cell count. In another aspect, a therapeutic composition comprises at most about $10^5$, $10^6$, $10^7$, $10^8$, $10^9$, $10^{10}$, $10^{11}$, $10^{12}$, $10^{13}$ or $10^{14}$ cfu or total cell count.

In another aspect, a therapeutic composition comprises at least about $10^5$, $10^6$, $10^7$, $10^8$, $10^9$, $10^{10}$, $10^{11}$, $10^{12}$, or $10^{13}$ cells or total cell count. In another aspect, a therapeutic composition comprises at most about $10^5$, $10^6$, $10^7$, $10^8$, $10^9$, $10^{10}$, $10^{11}$, $10^{12}$, $10^{13}$ or $10^{14}$ cells or total cell count.

In one aspect, a therapeutic composition is formulated as an oral capsule, microcapsule, tablet, or pill. In another aspect, a capsule, microcapsule, tablet, or pill is adapted for enteric delivery. In a further aspect, a capsule, microcapsule, tablet, or pill is an enteric capsule, microcapsule, tablet, or pill. In another aspect, a capsule, microcapsule, tablet, or pill comprises an enteric coating, is acid resistant, or both.

In one aspect, this application provides for the following embodiments:

Embodiment 1

A method for treating Parkinson's disease (PD) in a subject in need thereof, said method comprising administering to said subject a pharmaceutically active dose of a therapeutic composition comprising live non-pathogenic fecal bacteria or a non-cellular fecal filtrate.

Embodiment 2

The method of embodiment 1, wherein said subject further comprises a gastrointestinal disorder.

Embodiment 3

The method of embodiment 1, wherein said subject further comprises chronic constipation.

Embodiment 4

The method of embodiment 1, wherein said subject has a PD at a clinical stage selected from the group consisting of Stages I to V.

Embodiment 5

The method of embodiment 1, wherein said subject is an early stage PD patient.

Embodiment 6

The method of embodiment 1, wherein said subject exhibits one or more early signs of Parkinson's disease.

Embodiment 7

The method of embodiment 1, wherein said method reduces the rate of progression of PD in said subject.

Embodiment 8

The method of embodiment 1, wherein said method delays the need for symptomatic anti-Parkinsonian therapy in said subject.

Embodiment 9

The method of embodiment 1, wherein said composition comprises an isolated or purified population of said live non-pathogenic fecal bacteria.

Embodiment 10

The method of embodiment 1, wherein said composition comprises a non-selected fecal microbiota.

Embodiment 11

The method of embodiment 1, wherein said administration is on a daily basis.

Embodiment 12

The method of embodiment 1, wherein said administration lasts at least 1, 2, 3, 4, 5, 6, 7, 8, 9, or 10 weeks.

Embodiment 13

The method of embodiment 1, wherein said dose is administered at least once daily or at least once weekly for at least 2, 3, 4, 5, 6, 7, 8, 9, 10, 11, 12, 13, 14, or 15 consecutive days or weeks.

Embodiment 14

The method of embodiment 1, wherein said dose is administered at least once daily or at least once weekly for at least 1, 2, 3, 4, 5, 6, 7, 8, 9, 10, 11, or 12 consecutive weeks.

Embodiment 15

The method of embodiment 1, wherein said dose is administered at least once daily or at least once weekly for at most 3, 4, 5, 6, 7, 8, 9, 10, 11, 12, 13, 14, 15, 16, 17, 18, 19, or 20 consecutive days or weeks.

Embodiment 16

The method of embodiment 1, wherein said dose is administered at least once daily or at least once weekly for at most 1, 2, 3, 4, 5, 6, 7, 8, 9, 10, 11, or 12 consecutive weeks.

Embodiment 17

The method of embodiment 1, wherein said dose is administered at least twice daily or at least twice weekly for at least two consecutive days or weeks.

Embodiment 18

The method of embodiment 17, wherein said dose is administered at least twice daily or at least twice weekly for at least 3, 4, 5, 6, 7, 8, 9, 10, 11, 12, 13, 14, or 15 consecutive days or weeks.

Embodiment 19

The method of embodiment 17, wherein said dose is administered at least twice daily or at least twice weekly for at least 1, 2, 3, 4, 5, 6, 7, 8, 9, 10, 11, or 12 consecutive weeks.

Embodiment 20

The method of embodiment 17, wherein said dose is administered at least twice daily or at least twice weekly for at most 3, 4, 5, 6, 7, 8, 9, 10, 11, 12, 13, 14, 15, 16, 17, 18, 19, or 20 consecutive days or weeks.

Embodiment 21

The method of embodiment 17, wherein said dose is administered at least twice daily or at least twice weekly for at most 1, 2, 3, 4, 5, 6, 7, 8, 9, 10, 11, or 12 consecutive weeks.

Embodiment 22

The method of embodiment 1, wherein said dose is administered at least three times daily or at least three times weekly for at least one day or week.

Embodiment 23

The method of embodiment 22, wherein said dose is administered at least three times daily or at least three times weekly for at least 2, 3, 4, 5, 6, 7, 8, 9, 10, 11, 12, 13, 14, or 15 consecutive days or weeks.

Embodiment 24

The method of embodiment 22, wherein said dose is administered at least three times daily or at least three times weekly for at most 2, 3, 4, 5, 6, 7, 8, 9, 10, 11, 12, 13, 14, or 15 consecutive days or weeks.

Embodiment 25

The method of embodiment 1, wherein therapeutic composition comprising both live non-pathogenic fecal bacteria and a non-cellular fecal filtrate.

Embodiment 26

The method of embodiment 1, wherein therapeutic composition comprising live non-pathogenic fecal bacteria supplemented with a non-cellular fecal filtrate.

Embodiment 27

The method of embodiment 1, 25, or 26, wherein said non-cellular fecal filtrate comprises biologically active proteins or peptides, micronutrients, fats, sugars, small carbohydrates, trace elements, mineral salts, ash, mucous, amino acids, nutrients, vitamins, minerals, or any combination thereof.

Embodiment 28

The method of embodiment 1, 25, or 26, wherein said non-cellular fecal filtrate comprises one or more biologically active molecules selected from the group consisting of bacteriocin, lanbiotic, and lacticine.

Embodiment 29

The method of embodiment 1, 25, or 26, wherein said non-cellular fecal filtrate comprises one or more bacteriocins selected from the group consisting of colicin, troudulixine, putaindicine, microcin, and subtilosin A.

Embodiment 30

The method of embodiment 1, 25, or 26, wherein said non-cellular fecal filtrate comprises one or more lanbiotics selected from the group consisting of thuricin, nisin, subtilin, epidermin, mutacin, mersacidin, actagardine, and cinnamycin.

Embodiment 31

The method of embodiment 1, 25, or 26, wherein said non-cellular fecal filtrate comprises an anti-spore compound, an antimicrobial compound, an anti-inflammatory compound, or any combination thereof.

Embodiment 32

The method of embodiment 1, 25, or 26, wherein said non-cellular fecal filtrate comprises an interleukin, a cytokine, a leukotriene, an eicosanoid, or any combination thereof.

Embodiment 33

The method of any one of preceding claims, wherein said method comprises a first dosing schedule followed by a second dosing schedule.

Embodiment 34

The method of embodiment 33, wherein said second dosing schedule comprises a maintenance dose lower or equal to the dose of said first dosing schedule.

Embodiment 35

The method of embodiment 34, wherein said second dosing schedule lasts for at least about 2, 4, 6, 8, 10, 12, 18, 24, 36, 48, 72, or 96 months.

Embodiment 36

The method of embodiment 34, wherein said second dosing schedule lasts permanently.

Embodiment 37

The method of embodiment 33, wherein the interval between said first and second dosing schedules is at least about 1, 2, 3, 4, 5, 6, 7, 8, 9, 10, 11, or 12 weeks.

Embodiment 38

The method of embodiment 33, wherein said second dosing schedule is an continuous dosing schedule.

Embodiment 39

The method of embodiment 33, wherein said second dosing schedule is an intermittent dosing schedule.

Embodiment 40

The method of embodiment 39, wherein said intermittent dosing schedule comprises a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days.

Embodiment 41

The method of any one of preceding claims, wherein said composition is formulated as a delayed or gradual enteric release form.

Embodiment 42

The method of any one of preceding claims, wherein said administering comprises administering orally, by enema, or via rectal suppository.

Embodiment 43

The method of any one of preceding claims, wherein said composition is formulated as an enteric coated capsule, an acid-resistant, enteric-coated capsule, an enteric coated microcapsule, or formulated as part of a food, a food additive, a dairy-based product, a soy-based product or a derivative thereof, a jelly, or a yogurt.

Embodiment 44

The method of any one of preceding claims, wherein said method eliminates or reduces gastrointestinal dysbiosis.

Embodiment 45

The method of any one of preceding claims, wherein said method increase bacterial diversity in said subject's gastrointestinal tract.

Embodiment 46

The method of any one of preceding claims, wherein said pharmaceutically active dose comprises at least about 105, 106, 107, 108, 109, 1010, 1011, 1012, or 1013 cfu or total number of cells.

Embodiment 47

The method of embodiment 1, wherein said pharmaceutically active dose comprises at most about 105, 106, 107, 108, 109, 1010, 1011, 1012, or 1013 cfu or total number of cells.

Embodiment 48

The method of embodiment 1, wherein said pharmaceutically active dose is selected from the group consisting of from 105 to 1014, from 106 to 1014, from 107 to 1014, from 108 to 1014, from 109 to 1013, from 1010 to 1012, from 109 to 1014, from 109 to 1012, from 109 to 1011, from 109 to 1010, from 1010 to 1014, from 1010 to 1013, from 1011 to 1014, from 1011 to 1013, from 1012 to 1014, and from 1013 to 1014 cfu or total number of cells.

Embodiment 49

The method of embodiment 1, wherein said composition comprises a fecal microbiota further supplemented with a fecal microorganism.

Embodiment 50

The method of embodiment 49, wherein said fecal microorganism is selected from the group consisting of a *Bacteroides fragilis* ssp. *vulgatus*, *Collinsella aerofaciens*, *Bacteroides fragilis* ssp. *thetaiotaomicron*, *Peptostreptococcus productus* II, *Parabacteroides distasonis*, *Fusobacterium prausnitzii*, *Coprococcus eutactus*, *Collinsella aerofaciens* III, *Peptostreptococcus productus* I, *Ruminococcus bromii*, *Bifidobacterium adolescentis*, *Gemmiger formicilis*, *Bifidobacterium longum*, *Eubacterium siraeum*, *Ruminococcus torques*, *Eubacterium rectale*, *Eubacterium eligens*, *Bacteroides eggerthii*, *Clostridium leptum*, *Bacteroides fragilis* ssp. *A*, *Eubacterium biforme*, *Bifidobacterium infantis*, *Eubacterium rectale Coprococcus comes*, *Pseudoflavonifractor capillosus*, *Ruminococcus albus*, *Dorea formicigenerans*, *Eubacterium hallii*, *Eubacterium ventriosum* I, *Fusobacterium russi*, *Ruminococcus obeum*, *Eubacterium rectale*, *Clostridium ramosum*, *Lactobacillus leichmannii*, *Ruminococcus callidus*, *Butyrivibrio crossotus*, *Acidaminococcus fermentans*, *Eubacterium ventriosum*, *Bacteroides fragilis* ssp. *fragilis*, *Bacteroides AR*, *Coprococcus catus*, *Aerostipes hadrus*, *Eubacterium cylindroides*, *Eubacterium ruminantium*, *Eubacterium CH-1*, *Staphylococcus epidermidis*, *Peptostreptococcus BL*, *Eubacterium limosum*, *Tissirella praeacuta*, *Bacteroides L*, *Fusobacterium mortiferum* I, *Fusobacterium naviforme*, *Clostridium innocuum*, *Clostridium ramosum*, *Propionibacterium acnes*, *Ruminococcus flavefaciens*, *Ruminococcus AT*, *Peptococcus AU-1*, *Bacteroides fragilis* ssp. *ovatus*, -ssp. d, -ssp. f; *Bacteroides L-1, L-5*; *Fusobacterium nucleatum*, *Fusobacterium mortiferum*, *Escherichia coli*, *Gemella morbillorum*, *Finegoldia magnus*, *Peptococcus G, -AU-2*; *Streptococcus intermedius*, *Ruminococcus lactaris*, *Ruminococcus CO Gemmiger X*, *Coprococcus BH, -CC*; *Eubacterium tenue*, *Eubacterium ramulus*, *Bacteroides clostridiiformis* ssp. *clostridliformis*, *Bacteroides coagulans*, *Prevotella oralis*, *Prevotella ruminicola*, *Odoribacter splanchnicus*, *Desuifomonas pigra*, *Lactobacillus G*, *Succinivibrio A*, and a combination thereof.

Embodiment 51

The method of embodiment 10, wherein said fecal microbiota is further supplemented with bacterial spores.

Embodiment 52

The method of embodiment 51, wherein said bacterial spores are *Clostridium* spores or *Bacillus* spores.

Embodiment 53

The method of embodiment 10, wherein the preparation of said fecal microbiota involves a treatment selected from the group consisting of ethanol treatment, detergent treatment, heat treatment, irradiation, and sonication.

Embodiment 54

The method of embodiment 10, wherein the preparation of said fecal microbiota involves no treatment selected from the group consisting of ethanol treatment, detergent treatment, heat treatment, irradiation, and sonication.

Embodiment 55

The method of embodiment 10, wherein the preparation of said fecal microbiota involves a separation step selected from the group consisting of density gradients, filtration, and chromatography.

Embodiment 56

The method of embodiment 10, wherein the preparation of said fecal microbiota involves no separation step selected from the group consisting of density gradients, filtration, and chromatography.

Embodiment 57

The method of embodiment 10, wherein said fecal microbiota comprises a donor's entire fecal microbiota.

Embodiment 58

The method of embodiment 10, wherein said composition is substantially free of eukaryotic cells from said fecal microbiota's donor.

Embodiment 59

The method of embodiment 10, wherein said fecal microbiota is from reconstituted fecal material.

Embodiment 60

The method of embodiment 10, wherein said fecal microbiota is from synthetic fecal material.

Embodiment 61

The method of embodiment 10, wherein said fecal microbiota comprises no antibiotic resistant population.

Embodiment 62

The method of embodiment 10, wherein said fecal microbiota comprises a preparation of viable flora in proportional content that resembles a normal healthy human fecal flora.

Embodiment 63

The method of embodiment 10, wherein said fecal microbiota comprises bacteria from at least seven different families.

Embodiment 64

The method of embodiment 10, wherein said fecal microbiota has a Shannon Diversity Index of 0.4-5.0.

Embodiment 65

The method of embodiment 10, wherein said fecal microbiota comprises one or more microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium,* and *Monilia.*

Embodiment 66

The method of embodiment 10, wherein said fecal microbiota comprises no viable *Bacteroides, Fusobacterium, Propionibacterium, Lactobacillus, Ruminococcus, Escherichia coli, Gemmiger, Desulfomonas, Peptostreptococcus, Bifidobacterium, Monilia,* or any combination thereof.

Embodiment 67

The method of embodiment 10, wherein said fecal microbiota comprises one or more microorganisms selected from the group consisting of a *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus,* -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

Embodiment 68

The method of embodiment 1, wherein said composition comprises at least about 20%, 30%, 40%, 50%, 60%, 70%, 80%, 85%, 90%, 95%, 99%, or 99.5% bacterial spores.

Embodiment 69

The method of embodiment 1, wherein said composition is in a liquid, frozen, freeze-dried, spray-dried, foam-dried, lyophilized, or powder form.

Embodiment 70

The method of embodiment 1, wherein said composition comprises an excipient, a saline, a buffer, a buffering agent, or a fluid-glucose-cellobiose agar (RGCA) media.

Embodiment 71

The method of embodiment 1, wherein said composition comprises a cryoprotectant.

Embodiment 72

The method of embodiment 71, wherein said cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

Embodiment 73

The method of embodiment 1, wherein said composition further comprises an acid suppressant, an antacid, an H2 antagonist, a proton pump inhibitor or a combination thereof.

Embodiment 74

The method of embodiment 1, wherein said composition is substantially free of non-living matter.

Embodiment 75

The method of embodiment 1, wherein said composition is substantially free of acellular material selected from the group consisting of residual fiber, DNA, viral coat material, and non-viable material.

Embodiment 76

The method of embodiment 1, wherein said composition is formulated as an enteric coated capsule or microcapsule, an acid-resistant capsule or microcapsule, a powder suitable for reconstitution, a naso-duodenal infusion, or for delivery in the form of an enema or a colonoscopic infusion.

Embodiment 77

The method of embodiment 1, wherein said composition is administered together with a food, a liquid beverage, a food additive, a dairy-based product, a soy-based product or a derivative thereof, a jelly, or a yogurt.

Embodiment 78

The method of embodiment 1, wherein said subject is pretreated with an antibiotic prior to administration of said composition.

Embodiment 79

The method of embodiment 78, wherein said antibiotic is selected from the group consisting of rifabutin, clarithromycin, clofazimine, vancomycin, rifampicin, nitroimidazole, chloramphenicol, and a combination thereof.

Embodiment 80

The method of embodiment 78, wherein said antibiotic is selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof.

Embodiment 81

The method of any one of preceding claims, wherein said subject is pretreated with an anti-inflammatory drug prior to administration of said composition.

Embodiment 82

The method of any one of preceding claims, wherein said composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum*.

Embodiment 83

The method of embodiment 1, wherein said composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium*, and *Ruminococcus*.

Embodiment 84

The method of embodiment 1, wherein said composition comprises a plurality of purified, isolated, or cultured viable non-pathogenic microorganisms from one or more genera selected from the group consisting of *Clostridium, Collinsella, Coprococcus, Dorea, Eubacterium*, and *Ruminococcus*.

Embodiment 85

The method of embodiment 83, wherein said composition comprises two or more genera selected from the group consisting of *Collinsella, Coprococcus, Dorea, Eubacterium*, and *Ruminococcus*.

Embodiment 86

The method of embodiment 83, wherein said composition comprises two or more genera selected from the group consisting of *Coprococcus, Dorea, Eubacterium*, and *Ruminococcus*.

Embodiment 87

The method of embodiment 83 or 84, wherein said plurality of viable non-pathogenic microorganisms comprise one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale*, and *Ruminococcus torques*.

Embodiment 88

The method of any one of preceding claims, wherein said method eliminates or reduces one or more PD symptoms selected from the group consisting of tremor, slowed movement (bradykinesia), rigid muscles, impaired posture and balance, loss of automatic movements, speech changes, and writing changes.

Embodiment 89

The method of any one of preceding claims, wherein said method further comprises subjecting said subject to a symptomatic anti-Parkinsonian therapy.

Embodiment 90

The method of any one of preceding claims, wherein said method further comprises administering bromocriptine, benztropine, levodopa, ropinirole, pramipexole, rotigotine, cabergoline, entacapone, tolcapone, amantadine, selegiline or a combination thereof.

The method of embodiment 1, substantially as herein described and exemplified, and described with reference to the accompanying figures.

The disclosure may be better understood by reference to the following non-limiting Examples, which are provided as exemplary of the disclosure. The following examples are presented in order to more fully illustrate the preferred aspects of the disclosure and should in no way be construed, however, as limiting the broad scope of the disclosure. Therefore, the scope of the appended claims should not be limited to the description of the aspects contained herein.

EXAMPLES

Example 1. Preparation of Fecal Microbiota

Fecal microbiota is prepared essentially according to protocols published in US2014/0147417 or WO2014/152484. Summarized below is an exemplary protocol.

Potential fecal microbiota donors are screened according to a list of criteria used to exclude unsuitable donors. Potential fecal microbiota donors are excluded if they have received antibiotics, laxatives, diet pills, immunomodulators or chemotherapy in the preceding three months. Potential fecal microbiota donors are excluded if they have a history of all known infectious diseases, morbid obesity, diabetes, irritable bowel syndrome, inflammatory bowel disease, chronic diarrhea, constipation, colorectal polyps or cancer, a compromised immune system, metabolic syndromes, chronic fatigue syndrome, major GI surgery, or other diseases or conditions potentially associated with specific changes in fecal microbiota. Potential fecal microbiota donors are excluded if they exhibit positive laboratory tests for C-reactive protein, erythrocyte sedimentation rate, hepatitis A, hepatitis B, hepatitis C, human immunodeficiency virus, human T-lymphotropic virus or syphilis. Potential fecal microbiota donors are excluded if they exhibit a positive test for stool ova, parasites or viruses. Potential fecal microbiota donors are excluded if they engage in high-risk sexual behaviors, have been incarcerated, or received any tattoos or body piercings in areas that have had disease epidemics within the past three months.

Donor fecal material (fresh feces) is collected in a sterilized container, and then it is transferred to a blender. Approximately 500-1000 mL 0.9% saline solution is added to the blender and thoroughly mixed with the fecal sample. The resulting suspension is filtered at least 4 times through strainers prior to collecting a final suspension. The final suspension is centrifuged in 50 mL tubes at 1200×g for 3 minutes. The supernatant is discarded and the pellet is gently resuspended in approximately 50 mL of sterile 0.9% saline solution. The centrifugation and resuspension steps are repeated 2 to 4 additional times. Upon the final centrifugation, the supernatant is discarded. If the fecal microbiota is to be used immediately, the resultant pellet is resuspended in 1.5-volumes of 0.9% saline solution by gently mixing. If the fecal microbiota is to be stored, the resultant pellet is resuspended in 10% sterile glycerol and stored at −80 degrees Centigrade. If fecal microbiota are frozen, they are warmed to room temperature prior to administration to a patient. If fecal microbiota is lyophilized, the lyoprotectant formulation and lyophilization procedure follow essentially those described in US 2016/0331791, published Nov. 17, 2016.

Example 2: Oral Capsule Treatment Protocol (Short Regimen) for PD Patients with Bowel Dysfunction Patients are divided into four groups (Groups 1 to 4). Group 1 patients are administered a pre-treatment of antibiotics (e.g., Vancomycin, Metronidazole, and Colchicine) until the patient shows signs of improved bowel movements. Group 2 receives no antibiotics. Both Groups 1 and 2 receive a pre-colonoscopy bowel prep followed by capsule fecal microbiome therapy. Groups 3 and 4 receive no bowel prep while Group 3, not group 4, also receive an antibiotic pretreatment. Capsules are administered for 2 weeks as follows: two capsules (each containing $10^9$ to $10^{11}$ bacterial organisms), given twice-a-day for 4 days, two capsules twice-a-day every other day for 10 days. High dose capsules (total cell count of about $10^{12}$) are used in loading doses (also called treatment doses) for the initial 4 days. Lower dose capsules (total cell count of about 10) are used in maintenance doses for the subsequent 10 days. In patients receiving antibiotic pretreatment, capsules are administered one day after ceasing antibiotics. Patient symptoms are observed and clinical examination is performed before, during and post oral capsule treatment. Pre, during and post-treatment DNA metagenomics (2-4 days; 1 week; 6 weeks; 12 weeks) are also carried out.

Example 3: Oral Capsule Treatment Protocol (Intermediate Regimen) for PD Patients with Bowel Dysfunction Patients are divided into four groups (Groups 1 to 4). Group 1 patients are administered a pre-treatment of antibiotics (e.g., Vancomycin, Metronidazole, and Colchicine if constipation is an issue) until the patient shows signs of improved bowel movements. Group 2 receives no antibiotics. Both Groups 1 and 2 receive a pre-colonoscopy bowel prep followed by capsule fecal microbiome therapy. Groups 3 and 4 receive no bowel prep while Group 3, not group 4, also receive an antibiotic pretreatment. Capsules are administered for 18 weeks or more, as follows: two capsules twice-a-day for 14 days, two capsules twice-a-day every other day for 14 days, 4 capsules twice-a-week for 14 days, and 4 capsules once-a-week (e.g., each Monday) for 12 weeks. High dose capsules (total cell count of about $10^{12}$) are used in loading doses (also called treatment doses) for the initial 4 weeks. Lower dose capsules (total cell count of about $10^9$) are used in maintenance doses for the subsequent 14 weeks. In patients receiving antibiotic pretreatment, capsules are administered one day after ceasing antibiotics. Patient symptoms are observed and clinical examination is performed before, during and post oral capsule treatment. Pre, during and post-treatment DNA metagenomics (2-4 days; 1 week; 6 weeks; 12 weeks) are also carried out.

Example 4: Treatment of Patient with PD

A 59-year old patient with PD is treated with a fecal microbiome-based therapy based on acid resistant/delayed release double encapsulated oral capsules containing lyophilized donor-derived non-selected fecal microbiota. The patient's symptoms include severe bloating, severe urgency, stiffness in left arm, imbalance issues, inability to turn head whilst walking, and inability to focus. The patient experiences one bowel movement per day. The patient is subject to a 8-week treatment schedule which includes 10 fecal microbiome therapy liquid rectal enema infusions during a two week induction period, followed by 4 capsules (total cell count of each capsule: about $10^9$-$10^{12}$) per day during a 6 week maintenance treatment period. At week three post-initial treatment, the patient no longer experiences bloating, has increased energy, slight mobility in left arm, and is able to get out of bed without the use of prescribed PD medication. The patient continues to feel heart burn. The patient experiences 2 bowel movements per day. At week four post-initial treatment, the patient experiences seconds of urgency, is unable to get out of bed without prescribed PD medication, experiences PD symptoms, chalky patterns on palm of hands, and severe headaches. The patient experiences 2-3 bowel movements per day. At week five post-initial treatment, the patient experiences mild urgency, dry heaving, increased use of hand gestures, flatulence and burping, and overall improvement in movement (right arm insignificantly improved and left arm stiffness is still present). Patient's overall view on life has improved. The patient experiences one bowel movement per day. The Patient's condition remains improved at week 7 to a similar extent as in week 5. Patient ceases treatment due to a thyroidectomy at week 8.

Example 5: Treatment of Patient with PD

A 55-year old patient with PD is treated with a fecal microbiome-based therapy based on acid resistant/delayed release double encapsulated oral capsules containing lyophilized donor-derived non-selected fecal microbiota. The patient's symptoms include mild bloating, mild urgency, mild abdominal discomfort, sensory loss, tightness in throat. Patient experienced prior symptoms of sensory loss, tightness in throat, tremor in left ring finger, frozen left shoulder, prolonged cough, stiffness in left arm, severe constipation, pain prior to defecation, and tremor of left leg. The patient experiences two bowel movements per day. The patient is started on a 7 week treatment plan which includes 5 fecal microbiome colonscopic infusions during an induction period of 1 week and 4 capsules/day for 6 weeks during a maintenance period. At week 5 post initial fecal microbiome therapy, the patient experiences no bloating, abdominal discomfort, or urgency. Further some PD symptom improvements are also observed. For example, tremor in left leg and arm decreases. However, a decrease in balance is also observed. At week 6, no major improvements in PD symptoms are observed.

Example 6: Treatment of Patient with PD

A 60-year old patient with PD is treated with a fecal microbiome-based therapy. The patient's symptoms include speech, hand tremor, difficulty walking, and micrographic writing. The patient is prescribed with a 8 week treatment plan which includes 10 fresh fecal microbiome infusions during an induction period of 2 weeks and 4 capsules/day for 6 weeks during a maintenance period.

As various modifications could be made in the constructions and methods herein described and illustrated without departing from the scope of the disclosure, it is intended that all matter contained in the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entirety.

The invention claimed is:

1. A method for treating Parkinson's disease (PD) in a human subject in need thereof, the method comprising orally administering to the human subject one or more compositions comprising (i) a pharmaceutically active induction dose of a therapeutic composition comprising a fecal bacterial preparation comprising a community of live non-pathogenic fecal bacteria from a stool or portion thereof of a healthy human donor, and (ii) a second active agent, wherein the subject is further administered a maintenance dose of the therapeutic composition, wherein the maintenance dose is lower than the induction dose, wherein at least two doses of the therapeutic composition are administered to the subject over a two-week period, and wherein the human subject experiences an improvement in at least one symptom selected from the group consisting of tremor, slowed movement, rigid muscles, impaired posture and balance, loss of automatic movements, speech changes, and writing changes within 15 weeks after initiating treatment.

2. The method of claim 1, wherein the subject has PD at a clinical stage selected from the group consisting of Stages I to V.

3. The method of claim 1, wherein the therapeutic composition comprises a non-selected fecal microbiota.

4. The method of claim 3, wherein the fecal microbiota comprises a donor's substantially entire fecal microbiota.

5. The method of claim 1, wherein the fecal bacteria are from synthetic fecal material.

6. The method of claim 1, wherein the method reduces the rate of progression of one or more of the at least one symptom in the subject.

7. The method of claim 1, wherein the therapeutic composition is administered at least twice weekly for at least three weeks.

8. The method of claim 1, wherein the therapeutic composition is administered at least twice weekly for at least 4 weeks.

9. The method of claim 1, wherein the therapeutic composition is formulated as a delayed or gradual enteric release form.

10. The method of claim 1, wherein the therapeutic composition is in a liquid, frozen, freeze-dried, spray-dried, foam-dried, or powder form.

11. The method of claim 1, wherein the therapeutic composition comprises a cryoprotectant selected from the group consisting of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, and a combination thereof.

12. The method of claim 1, wherein the subject is pre-treated with an antibiotic prior to administration of the therapeutic composition.

13. The method of claim 1, wherein the second active agent comprises a non-fecal microbiome based therapy.

14. The method of claim 1, wherein the second active agent is selected from the group consisting of bromocriptine, benztropine, levodopa, ropinirole, pramipexole, rotigotine, cabergoline, entacapone, tolcapone, amantadine, and selegiline.

15. The method of claim 1, wherein the second active agent comprises levodopa, a dopamine agonist, an inhibitor of enzymes that inactivate dopamine, a monoamine oxidase B (MAO B) inhibitor, a catechol-O-methyl transferase (COMT) inhibitor, an anticholinergic, amantadine, or estrogen.

16. The method of claim 1, wherein the second active agent is a dopamine agonist.

17. The method of claim 1, wherein the second active agent is a monoamine oxidase B (MAO B) inhibitor.

18. The method of claim 1, wherein the second active agent is a catechol-O-methyl transferase (COMT) inhibitor.

19. The method of claim 1, wherein the second active agent is an anticholinergic.

20. The method of claim 1, wherein the second active agent comprises a bacterial isolate.

21. The method of claim 1, wherein the second active agent comprises purified bacteria belonging to a genus selected from the group consisting of: *Clostridium, Collinsella, Dorea, Ruminococcus, Coprococcus, Prevotella, Veillonella, Bacteroides, Bacillus* and a combination thereof.

22. The method of claim 1, wherein the induction dose is administered to the human subject twice-a-day for 4 days, and the maintenance dose is administered to the human subject twice-a-day every other day for 10 days.

23. The method of claim 1, wherein the therapeutic composition and the second active agent are in the same composition.

24. The method of claim 1, wherein the therapeutic composition and the second active agent are in different compositions.

* * * * *